United States Patent [19]

Curro et al.

[11] Patent Number: 4,609,518
[45] Date of Patent: Sep. 2, 1986

[54] MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES

[75] Inventors: John J. Curro; James C. Baird; Donald L. Gerth, all of Cincinnati; George M. Vernon, West Chester; E. Kelly Linman, Cincinnati, all of Ohio

[73] Assignee: The Procter & Gamble Company, Cincinnati, Ohio

[21] Appl. No.: 740,145

[22] Filed: May 31, 1985

[51] Int. Cl.⁴ .................. B29C 59/06; B29C 69/02
[52] U.S. Cl. .................... 264/504; 264/570; 425/71; 425/290; 425/326.1; 425/387.1; 425/388
[58] Field of Search ............. 264/504, 154, 156, 555, 264/556, 570; 425/290, 326.1, 387.1, 388, 71

[56] References Cited

U.S. PATENT DOCUMENTS

| | | | |
|---|---|---|---|
| RE. 23,910 | 12/1954 | Smith et al. | 18/19 |
| D. 278,468 | 4/1985 | Trotman et al. | D92/1.1 |
| 2,776,451 | 1/1957 | Chavannes | 18/10 |
| 2,809,392 | 10/1957 | Armstrong | 18/10 |
| 3,054,148 | 9/1962 | Zimmerli | 18/56 |
| 3,426,754 | 2/1969 | Bierenbaun et al. | 128/156 |
| 3,560,601 | 2/1971 | Johnson et al. | 264/93 |
| 3,802,972 | 4/1974 | Fleischer et al. | 156/7 |
| 3,911,187 | 10/1975 | Raley | 428/180 |
| 3,929,135 | 12/1975 | Thompson | 128/287 |
| 3,957,414 | 5/1976 | Bussey, Jr. et al. | 425/384 |
| 3,965,906 | 6/1976 | Karami | 128/287 |
| 3,966,383 | 6/1976 | Bussey, Jr. et al. | 425/388 |
| 3,979,494 | 9/1976 | Ericson | 264/154 |
| 3,989,867 | 11/1976 | Sisson | 428/132 |
| 3,994,299 | 11/1976 | Karami | 128/287 |
| 4,041,951 | 8/1977 | Sanford | 128/287 |
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,226,828 | 10/1980 | Hall | 264/555 |
| 4,248,822 | 2/1981 | Schmidt | 264/154 |
| 4,321,924 | 3/1982 | Ahr | 128/287 |
| 4,323,069 | 4/1982 | Ahr et al. | 128/287 |
| 4,327,730 | 5/1982 | Sorensen | 128/287 |
| 4,341,216 | 7/1982 | Obenour | 128/287 |
| 4,341,217 | 7/1982 | Ferguson et al. | 128/290 |
| 4,342,314 | 8/1982 | Radel et al. | 128/287 |
| 4,343,848 | 8/1982 | Leonard, Jr. | 428/156 |
| 4,351,784 | 9/1982 | Thomas et al. | 264/22 |
| 4,395,215 | 7/1983 | Bishop | 425/290 |
| 4,463,045 | 7/1984 | Ahr et al. | 428/131 |
| 4,477,502 | 10/1984 | O'Sullivan | 428/35 |
| 4,508,256 | 4/1985 | Radel et al. | 228/152 |
| 4,509,908 | 4/1985 | Mullane, Jr. | 425/290 |
| 4,518,643 | 5/1985 | Francis | 428/131 |

FOREIGN PATENT DOCUMENTS

845826 8/1960 United Kingdom .
1160625 8/1969 United Kingdom .

OTHER PUBLICATIONS

Commonly Assigned, Copending Patent Application Serial No. 623,274, filed on Jun. 21, 1984, in the name of Thomas Ward Osborne, III and entitled "Sanitary Napkin with Gross Foramina Overlying a Low Density, Resilient Structure".

Primary Examiner—Jan Silbaugh
Attorney, Agent, or Firm—E. Kelly Linman; John V. Gorman; Richard C. Witte

[57] ABSTRACT

A continuous, multi-phase process for debossing and perforating a substantially continuous web of substantially planar polymeric film to coincide with the image of one or more forming structures, each having a patterned forming surface with a multiplicity of holes and an opposed surface. Each forming structure is open from the holes in the forming surface to its opposed surface. The web of film has an indefinite length, a first surface, a second surface and a thickness. The thickness comprises the distance between the first surface and the second surface. The process comprises at least two sequential forming phases, one of which involves three-dimensional conformance of the web to the macroscopic profile of the forming structure and another of which involves aperturing of the web to coincide with fine-scale apertures in either the same or a separate forming structure. The order in which the phases are carried out will depend upon the properties desired in the resultant macroscopically expanded, three-dimensional, apertured polymeric web. Because the process is carried out in sequential phases, previously incompatible characteristics which could not be provided by prior art single-phase forming processes can now be achieved.

47 Claims, 40 Drawing Figures

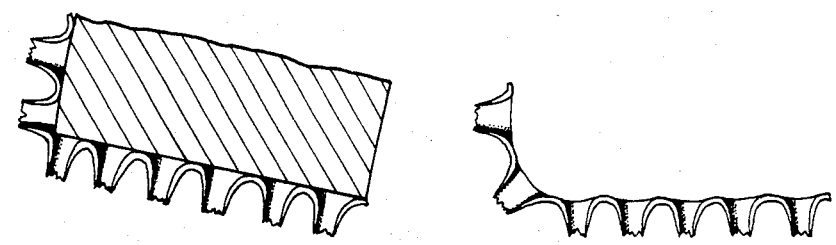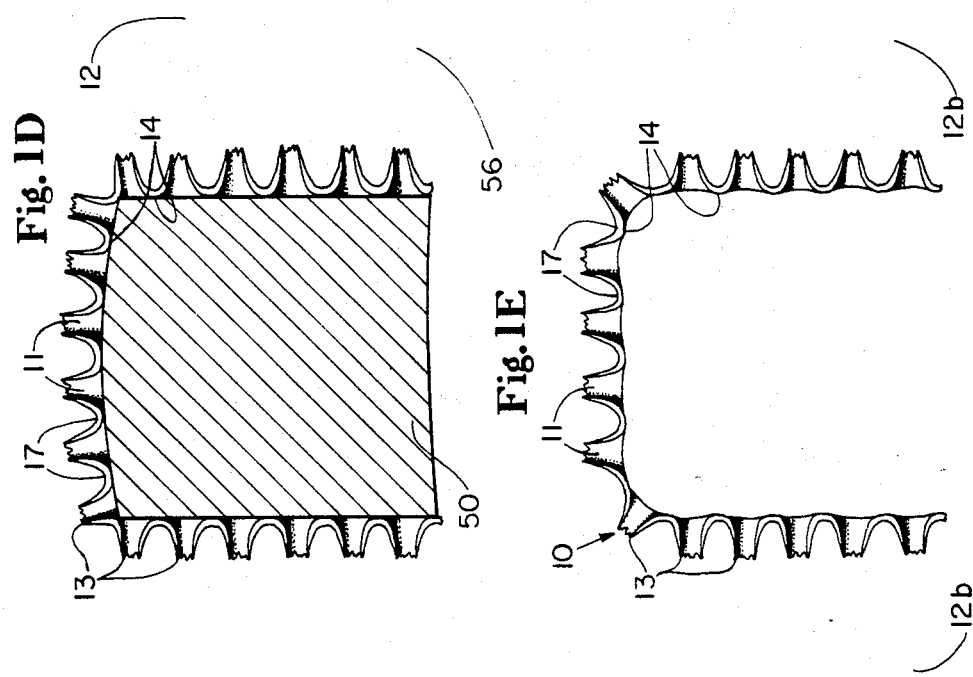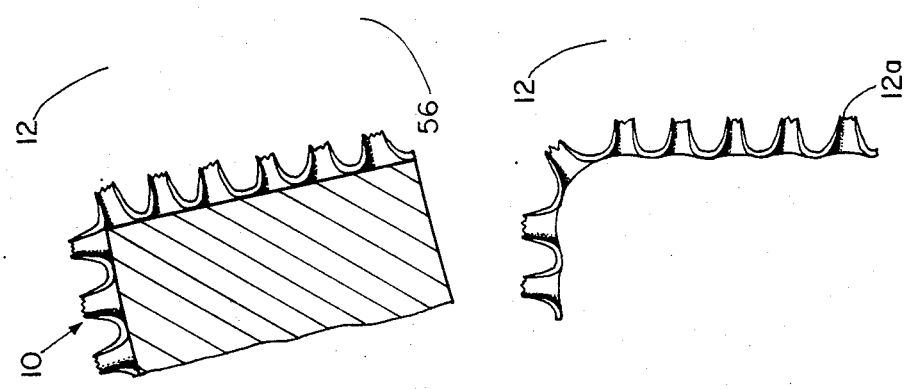

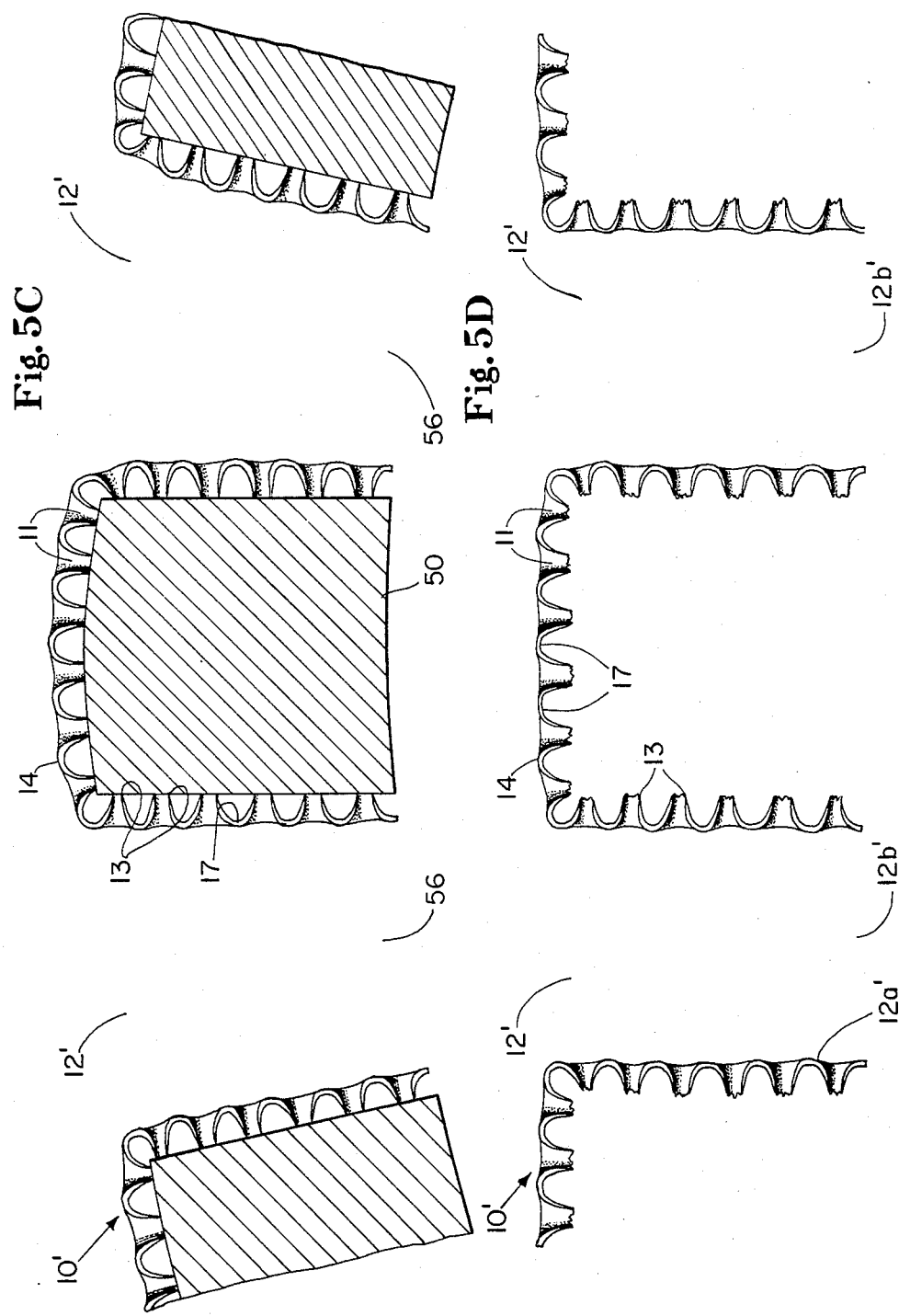

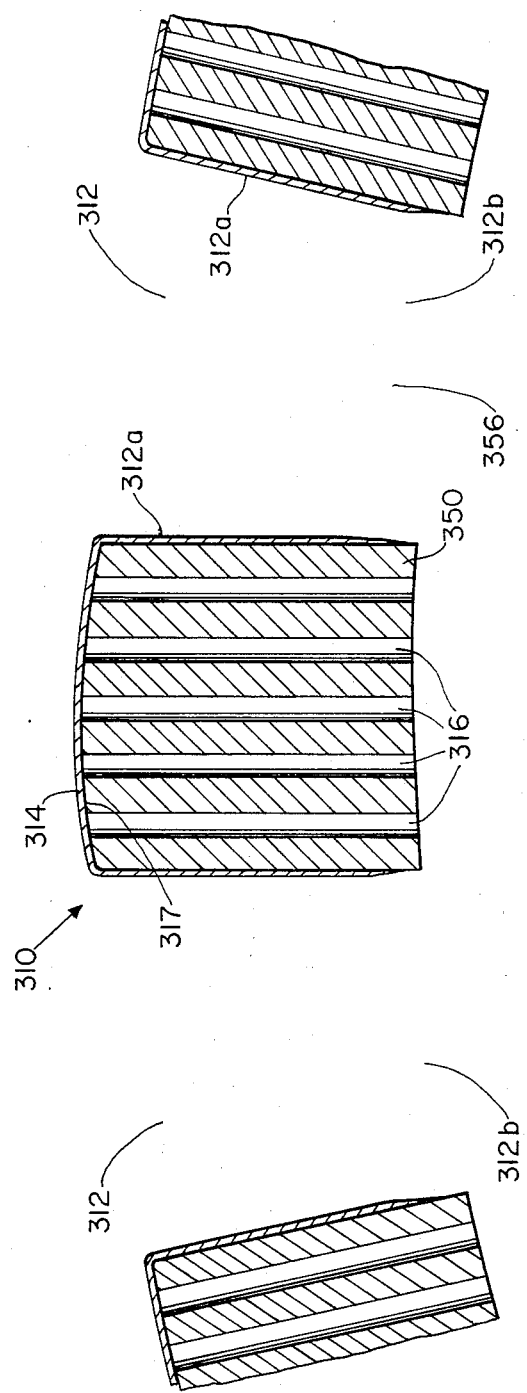

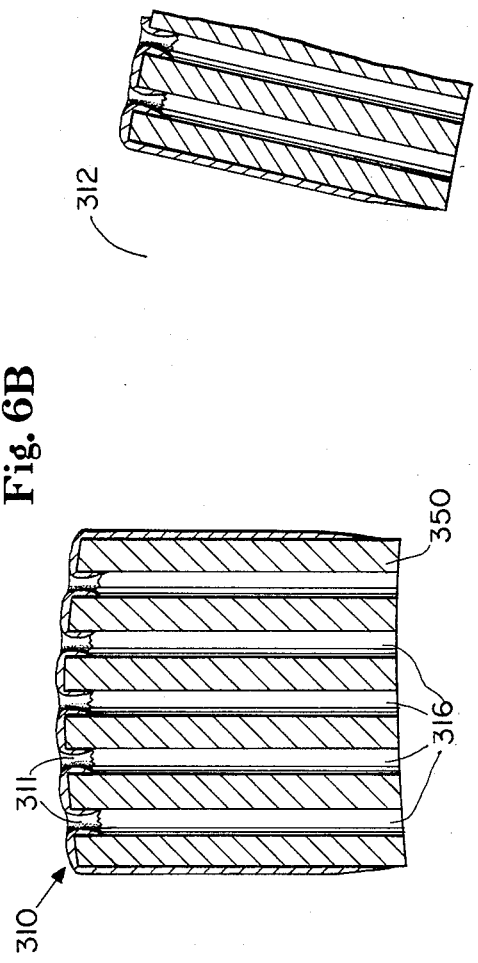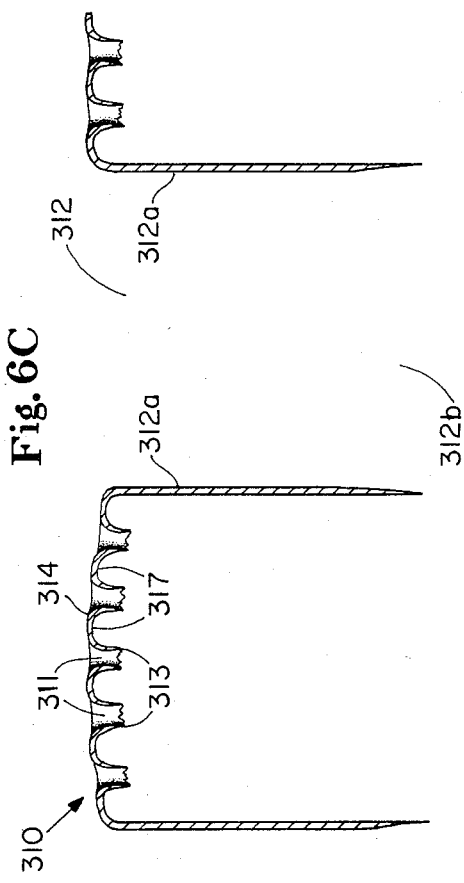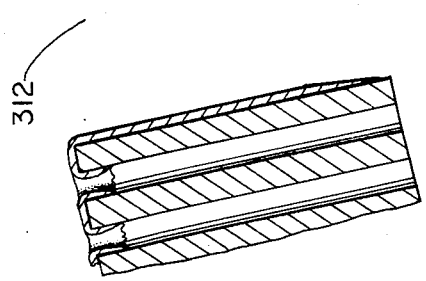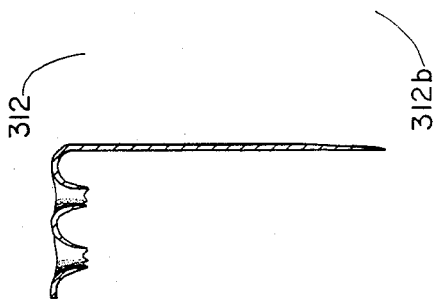

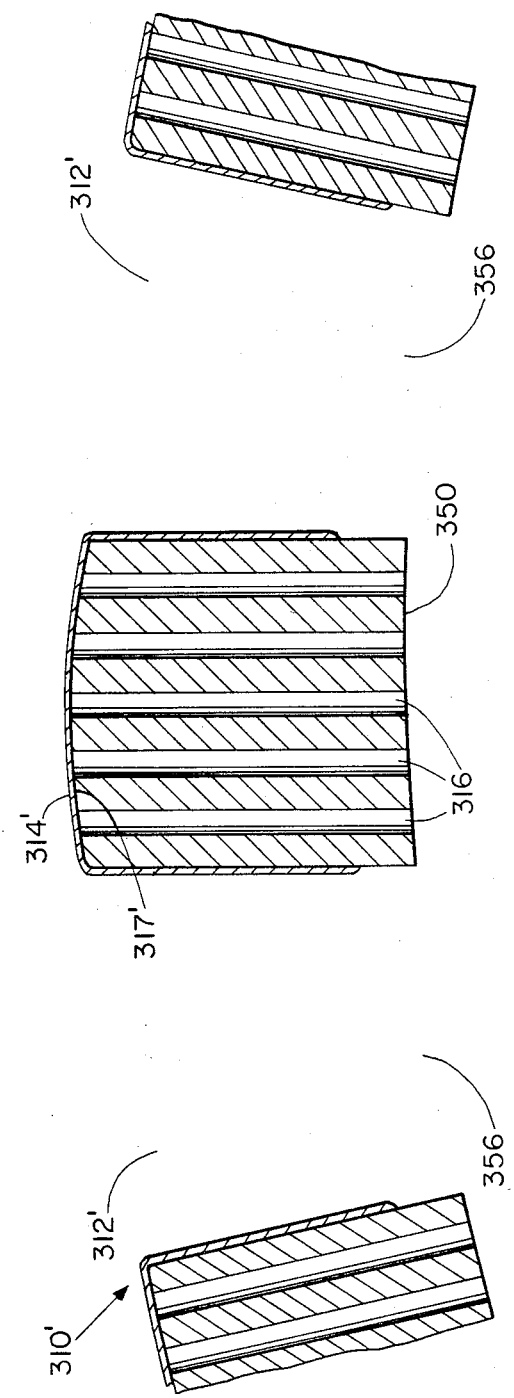

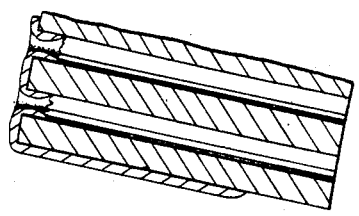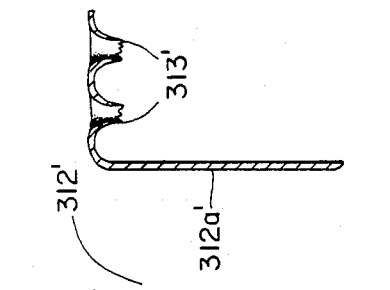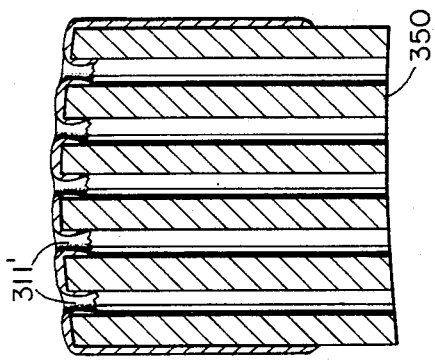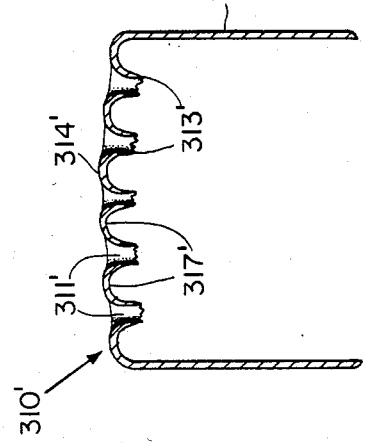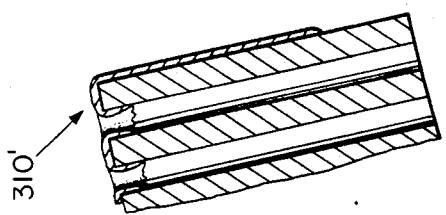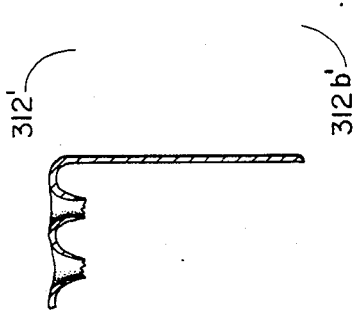
Fig. 8B
Fig. 8C

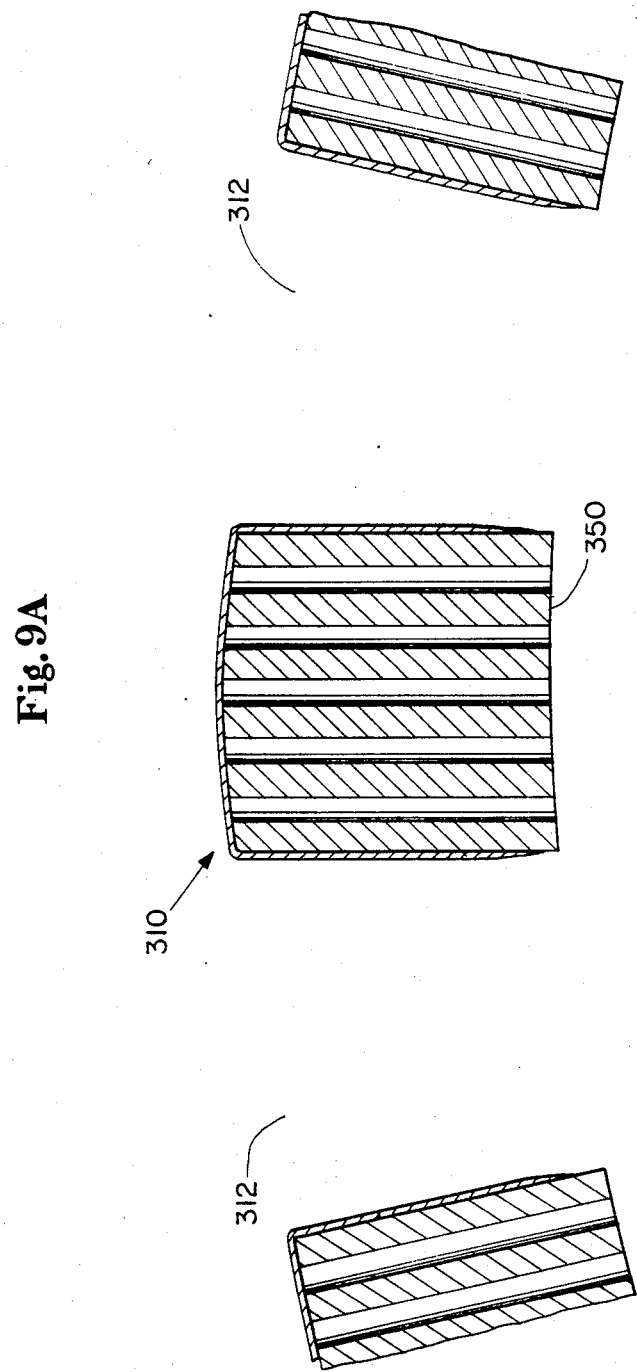

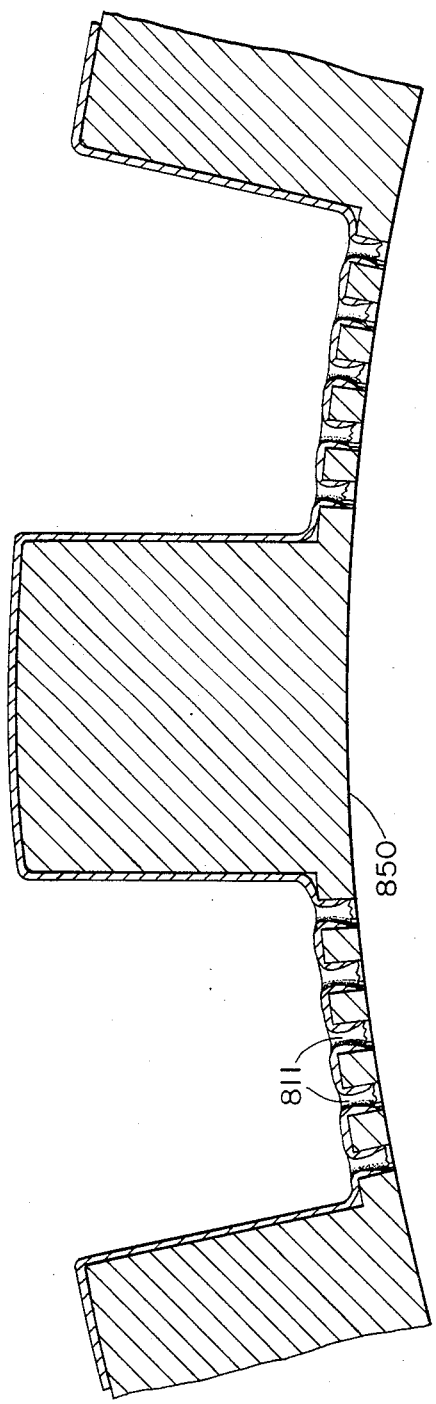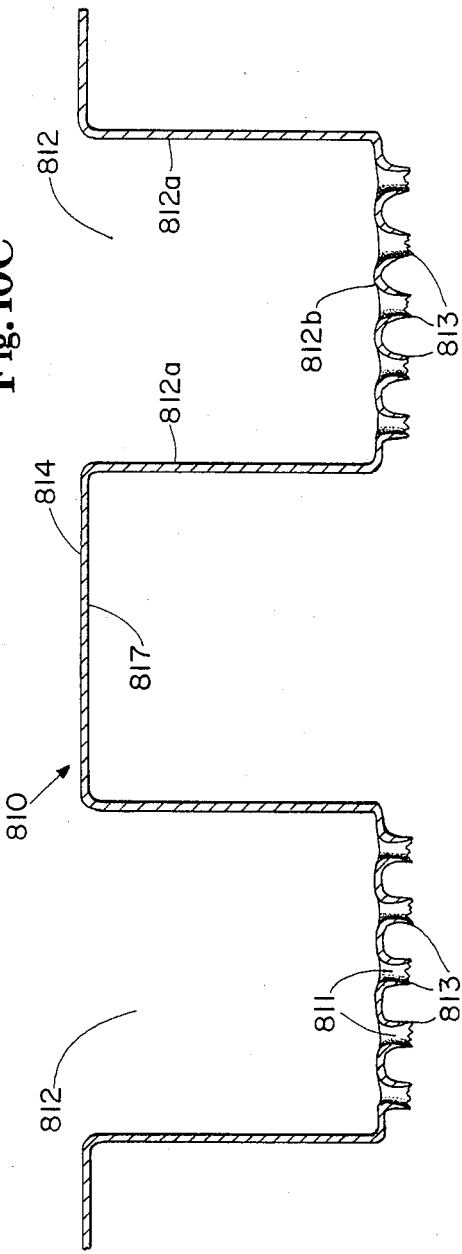

MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES

TECHNICAL FIELD

The present invention has relation to a multi-phase process for debossing and perforating a substantially continuous web of substantially planar polymeric film so as to coincide with the image of one or more three-dimensional forming structures.

The present invention has further relation to a multi-phase process for producing plastic webs which exhibit a combination of desirable attributes which were incompatible with one another when produced using single-phase forming processes of the prior art.

The present invention has further relation to a multi-phase forming process capable of producing macroscopically expanded, three-dimensional, apertured polymeric webs comprised of materials which could not be effectively processed on single-phase forming processes of the prior art.

The present invention has further relation to a multi-phase forming process which is capable of reliable, high-speed, continuous operation, thereby greatly reducing the cost of the unique plastic webs produced by said process.

The present invention has still further relation to a multi-phase forming process for producing macroscopically expanded, three-dimensional, apertured plastic webs exhibiting highly desirable fluid and vapor transmission capabilities in addition to visual and tactile impressions which are actually preferred by consumers over woven and nonwoven fibrous webs when worn in contact with the skin.

BACKGROUND ART

Macroscopically expanded, three-dimensional, apertured polymeric webs are generally known in the art.

As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to the naked eye when the perpendicular distance between the viewer's eye and the plane of the web is about 12 inches. By way of contrast, the term "planar", when utilized herein to describe plastic webs, ribbons and films, refers to the overall condition of the web, ribbon or film when viewed by the naked eye on a macroscopic scale. In this context "planar" webs, ribbons and films may include webs, ribbons and films having fine-scale surface aberrations on one or both sides, said surface aberrations not being readily visible to the naked eye when the perpendicular distance between the viewer's eye and the plane of the web is about 12 inches or greater.

One macroscopically expanded, three-dimensional, apertured plastic web which is particularly well suited to transferring fluid deposited on one surface thereof to its opposite surface and thereafter isolating the transferred fluid from the wearer's skin is disclosed in commonly assigned U.S. Pat. No. 3,929,135 issued to Thompson on Dec. 30, 1975, and hereby incorporated herein by reference. Thompson describes a macroscopically expanded, three dimensional topsheet comprised of liquid impermeable material, but provided with a pattern of tapered capillaries, said capillaries having a base opening in the plane of the topsheet and an apex opening remote from the plane of the topsheet, said apex opening being in intimate contact with the absorbent pad utilized in the disposable absorbent bandage. The Thompson topsheet allows the free transfer of fluids from the wearer's body into the absorbent element of the device while inhibiting the reverse flow of these fluids. This provides a relatively much drier surface in contact with the user than had previously been obtainable.

Another macroscopically expanded, three-dimensional, apertured plastic web well suited for use as a topsheet on absorbent bandages such as sanitary napkins is disclosed in commonly assigned U.S. Pat. No. 4,342,314 issued to Radel and Thompson on Aug. 3, 1982, said patent being hereby incorporated herein by reference. The macroscopically expanded, three-dimensional plastic web disclosed in the Radel and Thompson patent exhibits a fiber-like appearance and tactile impression which has been favorably received by consumers when used as a wearer contacting surface.

According to the teachings of the aforementioned commonly assigned patents to Thompson and to Radel et al., plastic webs of the aforementioned type can be made by applying a fluid pressure differential to the web while it is supported on a three-dimensional forming structure until the web is macroscopically expanded to comply with the three-dimensional cross-section of the forming structure on which it is supported. When aperturing of the macroscopically expanded, three-dimensional web is desired, said fluid pressure differential is applied continuously until such time as aperturing of the web in areas coinciding with the apertures in the forming structure has been completed.

While single-phase forming processes of this general type have been successfully utilized in producing macroscopically expanded, three-dimensional, apertured plastic webs exhibiting many characteristics generally viewed as favorable by consumers, the majority of such single-phase processing techniques have been unable to deliver all of the desired characteristics in a single finished web structure, particularly at high production speeds.

OBJECTS OF THE INVENTION

Accordingly, it is an object of the present invention to provide a process wherein various combinations of previously incompatible characteristics can be provided in a single macroscopically expanded, three-dimensional, apertured polymeric web.

It is another object of the present invention to provide macroscopically expanded, three-dimensional apertured plastic webs which offer improved fluid and vapor handling characteristics along with highly preferred appearance, softness and tactile impression when compared to woven and nonwoven fibrous structures.

It is still another object of the present invention to provide high-speed, reliable, multi-phase process and apparatus for debossing and perforating a substantially continuous web of substantially planar polymeric material to coincide with the image of one or more forming structures used in the process.

It is still another object of the present invention to provide multi-phase process and apparatus for producing macroscopically expanded, three-dimensional, apertured plastic webs wherein the different phases of the process may be separated from one another either temporally or spatially or both.

It is still another object of the present invention to provide such multi-phase process and apparatus, wherein the latter phases of the process may be so selected as not to alter either the solid state molecular structure of the web or any of the characteristics imparted to the web by earlier phases of the process.

DISCLOSURE OF THE INVENTION

The present invention pertains, in a particularly preferred embodiment, to a multi-phase method of making debossed and apertured polymeric webs which exhibit three-dimensional geometric forms, a number of which were at best difficult and at worst impossible to make using single-phase forming processes of the prior art. Specifically, multi-phase processes of the present invention are capable of forming a film with very small and very large apertures or capillary networks immediately adjacent one another while accurately replicating the macroscopic, three-dimensional cross-section of the forming structure. In addition, it permits the formation of macroscopically expanded, three-dimensional, apertured plastic webs exhibiting a very large overall caliper in conjunction with very tiny apertures either in the land areas of the web or in the end walls of the capillary networks or both. Capillary networks having tiny apertures in their sidewalls may also be produced using embodiments of the present multi-phase process. In yet other preferred embodiments, webs exhibiting capillary networks having sidewalls extending in opposite directions from one another may also be produced.

In one preferred embodiment of the present process, a web of molten polymeric resin is extruded directly onto a perforate, three-dimensional forming structure and subjected to a fluid pressure differential, typically vacuum. This phase of the operation provides good conformation of the web to the forming structure and imparts significant overall caliper to the web. Those portions of the web coinciding with a multiplicity of macroscopic cross-section apertures in the forming structure will also be apertured during this phase of the forming process. The molten web is thereafter cooled while still subject to the forming vacuum to prevent spring-back and consequent loss of caliper. At lower production speeds, e.g., below about 50 feet per minute, web cooling is often carried out simply by the flow of air through or against the film, while at higher production speeds it is generally desirable to accelerate the cooling process by applying a low pressure water spray or the like. The film is then transported while on the same forming structure to a second forming phase, preferably comprising a high pressure liquid jetting operation, which provides aperturing of the web not only in those areas coinciding with the very small apertures present in the forming structure, but also in any as yet unapertured areas of the web coinciding with any of the macroscopic cross-section apertures in the forming structure. If desired, the macroscopically expanded web can be fed to the high pressure liquid jetting operation while it is still subject to the forming vacuum used in the initial phase of the process. In this situation, the high pressure liquid jet not only provides aperturing of the web in those areas coinciding with the very small apertures present in the forming structure, but may also afford some additional web cooling benefits.

While the present invention may take many different executional forms, multi-phase web forming processes of the present invention comprise at least two discrete forming phases, each of which utilizes a fluid pressure differential to achieve its objective. One of the phases involves macroscopically conforming the polymeric web to the macroscopic cross-sectional profile of the forming structure on which it is supported while subject to one of the fluid pressure differentials. Substantial aperturing of the web in those areas coinciding with the macroscopic cross-section apertures in the forming structure usually occurs during this phase of the process. The other phase of the forming process also involves applying a fluid pressure differential to the plastic web. However, this phase is less concerned with macroscopically expanding the web to conform it to the three-dimensional cross-section of the forming structure. Rather, its primary objective is to fully aperture the web in all areas coinciding with apertures in the forming structure, including very fine apertures in the non-debossed land areas of the web and/or the end walls of the larger capillary networks formed therein.

The order in which these discrete forming phases are applied will depend upon the particular characteristics desired in the resultant macroscopically expanded, three-dimensional, apertured polymeric web.

The discrete forming phases may be utilized on a single forming structure including all of the features desired in the resultant web or on multiple forming structures, each of which imparts only a portion of the desired features to the web.

The fluid media applied during each of the forming phases of the present invention may be similar or dissimilar to one another, again depending upon the particular characteristics desired in the resultant polymeric web.

Because the process variables for each discrete phase of the forming process can be optimized to achieve a precise result, macroscopically expanded, three-dimensional, apertures polymeric webs can be made to exhibit combinations of characterists which were previously thought to be incompatible with one another due to limitations inherent in prior art single-phase forming processes.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 1D is a greatly enlarged inset of the polymeric web after it has been fed onto a second forming structure exhibiting a macroscopic, three-dimensional cross-sectional profile so that its opposite surface is in contact with the second forming structure, said polymeric web having thereafter been subjected to a second fluid pressure differential;

FIG. 1E is a greatly enlarged inset of the polymeric web after completion of the two-phase forming process generally illustrated in FIG. 1;

FIG. 5C is a greatly enlarged inset showing the condition of the web after it has been removed from the first forming structure and fed onto a second macroscopic cross-section forming structure without reversing its orientation, said web having thereafter been subjected to a second fluid pressure differential;

FIG. 5D is a greatly enlarged inset showing the resultant web after completion of the two-phase forming process generally disclosed in FIG. 5;

FIG. 6A is a greatly enlarged inset showing the condition of the polymeric web after it has been subjected to vacuum forming and water assisted cooling;

FIG. 6B is a greatly enlarged inset showing the condition of the polymeric web after it has been subjected to a higher pressure liquid jetting process while supported on the same forming structure on which the vacuum forming process was carried out; and FIG. 6C is a greatly enlarged inset showing the resultant web after the two-phase forming process generally illustrated in FIG. 6 has been completed;

FIG. 8A is a greatly enlarged inset showing the condition of the polymeric web after it has been subjected to a first high pressure liquid jetting operation on a forming structure of the type generally illustrated in FIG. 7;

FIG. 8B is a greatly enlarged inset showing the condition of the web after it has been subjected to a second, higher pressure jetting operation while supported on the same forming structure on which the first liquid jetting operation was carried out;

FIG. 8C is a greatly enlarged inset showing the resultant polymeric web after the two-phase forming process shown in FIG. 8 has been completed;

FIG. 9A is a greatly enlarged inset showing the condition of the web after it has been subjected to a first fluid pressure differential comprising suction applied adjacent the innermost surface of the forming structure;

FIG. 10B is greatly enlarged inset showing the condition of the web after it has been subjected to a second fluid pressure differential comprising a high pressure liquid jet while still subject to the influence of the forming vacuum;

FIG. 10C is a greatly enlarged inset showing the resultant web after completion of the two-phase forming process generally illustrated in FIG. 10;

DETAILED DESCRIPTION OF THE PRESENT INVENTION

While the present invention will be described in the context of providing macroscopically expanded, three-dimensional, apertured plastic webs particularly suited for use as a wearer contacting surface on absorbent bandages such as disposable diapers, sanitary napkins, wound dressings and the like, the present invention is in no way limited to such applications. To the contrary, the present invention may be practiced to great advantage whenever it is desired to produce plastic films or webs exhibiting properties, characteristics, aesthetics, fineness of detail etc. not previously obtainable using prior art single-phase web forming processes. The patterns created may be of any desired shape, they may be regulated or random, reticulated or non-reticulated, continuous or interrupted, or any desired combination thereof. The detailed description of the structures disclosed herein and their suggested use as topsheets and/or backsheets in a disposable absorbent bandage context will allow one skilled in the art to readily adapt the invention to produce webs well suited to other applications.

Figure 1A:
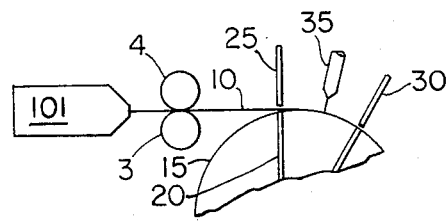
FIG. 1A is a partial illustration of a variation of the process generally shown in FIG. 1, wherein the supply roll of substantially planar polymeric film is replaced by an extruder which extrudes a web of molten resin onto the first forming structure.
Figure 1B:
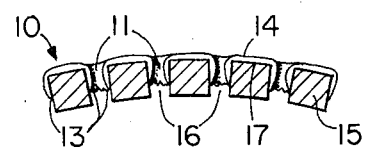
FIG. 1B is a greatly enlarged inset showing, in simplified terms, the condition of the polymeric web after it has been subjected to a first fluid pressure differential on the first forming structure.
Figure 1:
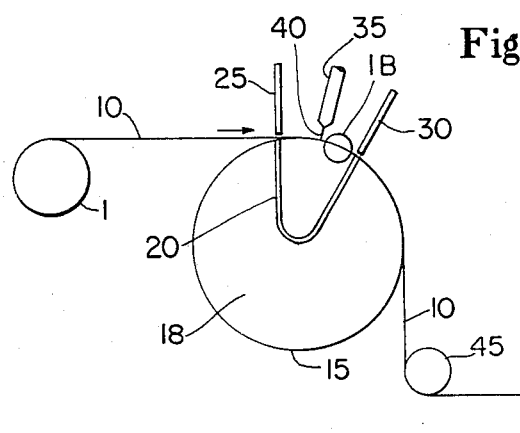
FIG. 1 is a simplified schematic illustration of a two-phase film forming process of the present invention.

A particularly preferred multi-phase, continuous forming process of the present invention is schematically illustrated in FIG 1. In the embodiment shown in FIG. 1, a web of substantially planar film 10 comprised of a polymeric material such as polyethylene is fed from a supply roll 1 onto the surface of a first forming drum 18 about which a forming structure 15 continuously rotates at substantially the same speed as the incoming web. The forming drum 18 preferably includes an internally located vacuum chamber 20 which is preferably stationary relative to the moving forming structure 15. A pair of stationary baffles 25, 30 approximately coinciding with the beginning and the end of the vacuum chamber 20 are located adjacent the exterior surface of the forming structure. Intermediate the stationary baffles 25, 30 there is preferably provided means for applying a fluid pressure differential to the substantially planar web of polymeric film 10 as it passes across the suction chamber. In the illustrated embodiment, the fluid pressure differential applicator means comprises a high pressure liquid nozzle 35 which discharges a jet of liquid 40, such as water, substantially uniformly across the entire width of the web 10. Details as to the construction, positioning and operating pressure of liquid nozzle 35 are fully set forth in the commonly assigned U.S. patent application of John J. Curro, Alan J. Trusty and George M. Vernon, Ser. No. 580,911, filed Feb. 16, 1984 and entitled FORMED MATERIAL PRODUCED BY SOLID-STATE FORMATION WITH A HIGH-PRESSURE LIQUID STREAM, said patent application being hereby incorporated herein by reference.

Figure 2:
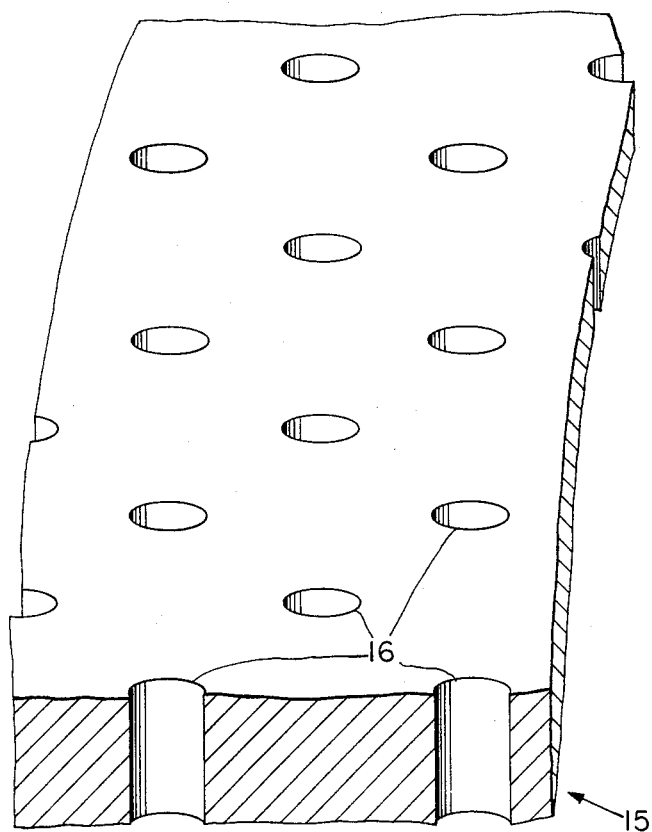
FIG. 2 is a greatly enlarged fragmentary view of the first forming structure utilized to support the polymeric web when the web is subjected to a first fluid pressure differential generally in accordance with the process illustrated in FIG. 1.

Forming structure 15, a greatly enlarged fragmentary segment of which is illustrated in FIG. 2, includes a multiplicity of relatively small apertures 16 across all or any desired portion of its surface. For disposable diaper topsheet applications these apertures typically range in size between about 1 mil and about 10 mils in diameter. Their spacing may be in a regular pattern or it may vary randomly, as desired, in the resultant web. Methods of constructing suitable three-dimensional tubular forming members of this general type are disclosed in commonly assigned U.S. Pat. No. 4,508,256 issued to Radel et al. on Apr. 2, 1985 and commonly assigned U.S. Pat. No. 4,509,908 issued to Mullane, Jr. on Apr. 9, 1985, said patents being hereby incorporated herein by reference.

The apertures 16 in the forming structure 15 may be of any desired shape or cross-section when the forming structure is fabricated utilizing the laminar construction techniques generally disclosed in the aforementioned commonly assigned patents.

Alternatively, the tubular shaped forming structure 15 may be comprised of non-laminar construction and the desired pattern of apertures 16 created by means of laser drilling or the like. It is also possible to use belts or the like comprised of pliable material and operating continuously about a pair of rolls. In the latter circumstance it is generally desirable to provide suitable support beneath the pliable belt when it is subjected to the fluid pressure differential to avoid distortion.

Figure 3:
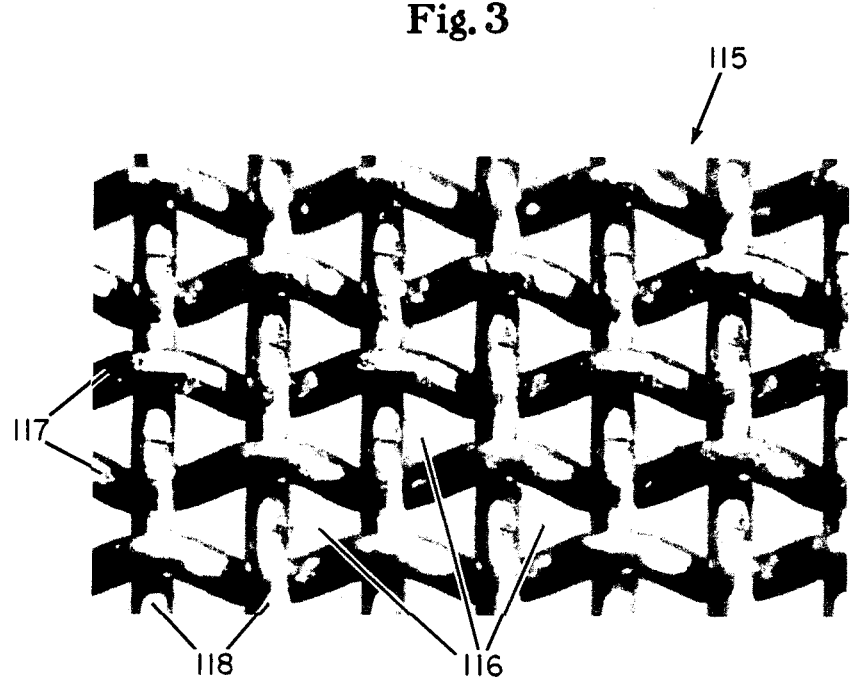
FIG. 3 is a greatly enlarged photograph of a fragment of an alternative forming structure which could be utilized when the polymeric web is subjected to the first fluid pressure differential generally illustrated in FIG. 1.

Still another suitable forming structure which can be used to provide fine-scale aperturing of the polymeric web 10 comprises a woven wire mesh 115, such as that shown in the highly enlarged fragmentary photograph of FIG. 3. In this situation a multiplicity of intersecting filaments 117 and 118 are interwoven with one another to provide a knuckle pattern, such as that generally shown in FIG. 3, about the surface of the forming structure 115. The woven wire mesh filaments may be comprised of metal or polymeric material. Woven wire mesh forming structures 115 having filaments 117, 118 ranging in diameter from about 3 mils to about 7 mils and mesh counts ranging from about 140 by 140 per square inch to about 80 by 80 per square inch, respectively, will typically produce very soft feeling apertured webs when subjected to the high pressure liquid jet 40 issuing from nozzle 35, as generally shown in FIG. 1. The relatively small apertures created in such webs substantially correspond to the void spaces created in the interstices 116 between the intersecting filaments.

As will be appreciated by those skilled in the art, the degree of conformance of the polymeric web 10 to the surface of the forming structure 15 and the size of the apertures created therein will be influenced by factors such as the temperature of the film 10 at the time it is subjected to the liquid jet 40, the pressure at which the jet 40 is applied to the surface of the film, the temperature of the liquid comprising the jet, the mass flux of the liquid jet, etc.

In general, when the fluid pressure differential applied to the web is in the form of vacuum, the higher the temperature of the incoming film 10, the greater will be the degree of conformance and aperturing. However, when the fluid pressure differential applied to the web is in the form of a high pressure liquid jet, as is the case in FIG. 1, it is generally preferred that the incoming web be in a solid rather than a molten state. In the case of the embodiment shown in FIG. 1A, a web of molten resin 10 extruded from a conventional extruder 101 could be fed between a pair of chill rolls 3,4 prior to being fed onto the forming structure 15 to substantially cool the resin before it passes beneath liquid jet 40.

Whatever the origin of the incoming web of polymeric material 10, after it passes beneath the liquid jet 40, its condition will be generally as shown in the greatly enlarged inset of FIG. 1B. At this point, fine-scale apertures 11 corresponding to the relatively small apertures 16 in forming structure 15 have been created in the film 10. The small volcano-like cusps 13 formed about the edge of each aperture 11 reflect a degree of thinning of the film just prior to rupture.

Figure 1C:
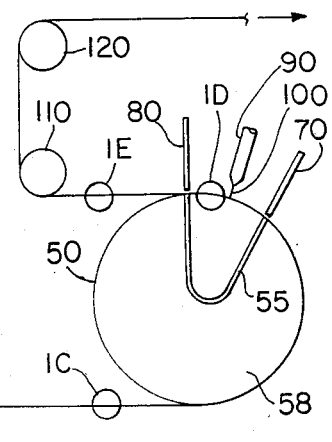
FIG. 1C is a greatly enlarged inset of the polymeric web after it has been removed from the first forming structure.
Figure 1C:
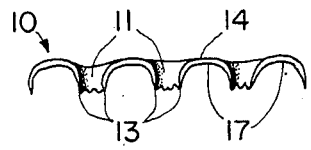

Following application of the first fluid pressure differential to the film, the finely apertured polymeric web 10 is removed from the surface of the first fine-scale forming structure 15 about an idler roll 45 in the condition illustrated in greatly enlarged form in the inset of FIG. 1C. Because of the presence of the cusps 13 surrounding each of the tiny apertures 11, the surface 17 which contacted forming structure 15 exhibits a much softer tactile impression than the surface 14 which was contacted by the liquid jet 40. Accordingly, surface 17 of the web is generally preferred as a wearer contacting surface over surface 14.

After completion of the first phase of the web forming process disclosed in FIG. 1, the finely apertured web 10 may be fed to the second phase of the forming process for macroscopic expansion or to a rewind station for temporary storage. In the latter circumstance, application of the second phase of the process may be deferred until a later date, perhaps at a different location.

Alternatively, the finely apertured web 10 may be utilized without further processing in an end product wherein fluid permeability and a soft tactile impression are particularly desirable, but a macroscopically expanded, three-dimensional cross-section is not essential.

Because of the desirable tactile impression imparted to surface 17 of the web 10 in the embodiment illustrated in FIG. 1, a web which is to undergo macroscopic, three-dimensional expansion is preferably fed onto a second forming structure 50 which operates about forming drum 58 so that its opposite surface 14 is placed in contact with forming structure 50. Forming drum 58, which is generally similar to forming drum 18 also includes a stationary vacuum chamber 55 located adjacent the interior of forming structure 50. Stationary baffles 70 and 80 substantially coincide with the leading and trailing edges of the vacuum chamber 55, thereby defining a second fluid pressure differential zone wherein a second liquid nozzle 90, generally similar to liquid nozzle 35, is positioned. Liquid nozzle 90 also discharges a relatively high pressure liquid jet 100 against the surface 17 of web 10 as it passes therebeneath.

Because the macroscopic cross-section of forming structure 50 is considerably different than that of forming structure 15, the pressure and mass flux rates of nozzle 90 are preferably adjusted independently of the pressure and mass flux rates used for nozzle 35. Additional details as to the construction, positioning and operating pressure of liquid nozzle 95 may be found in the commonly assigned, co-pending U.S. patent application of John J. Curro, Alan J. Trusty and George M. Vernon, Ser. No. 580,911, filed Feb. 16, 1984 and entitled FORMED MATERIAL PRODUCED BY SOLID-STATE FORMATION WITH A HIGH-PRESSURE LIQUID STREAM, said patent application being incorporated herein by reference.

Figure 4:
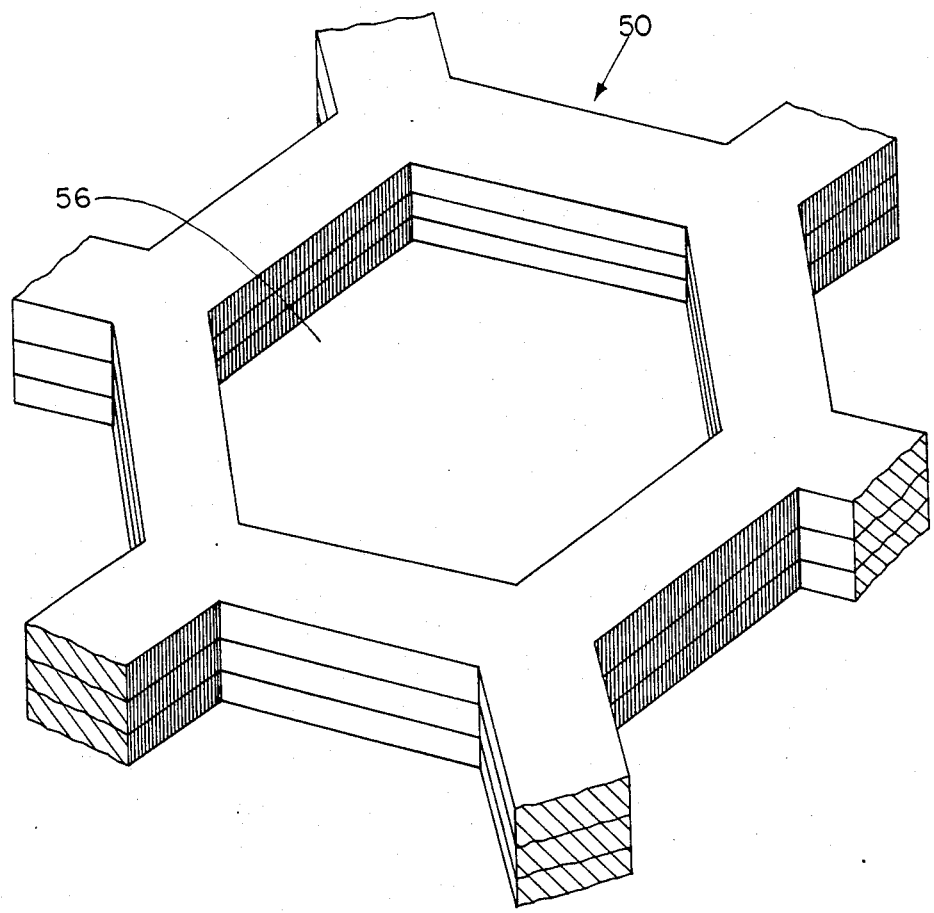
FIG. 4 is a greatly enlarged fragmentary view of the forming structure on which the polymeric web is supported during application of the second fluid pressure differential generally illustrated in FIG. 1.

The macroscopic cross-section of forming structure 50 is visible in the greatly enlarged fragmentary perspective of FIG. 4. As is more readily apparent from the inset of FIG. 1C, the web of film 10 containing fine-scale apertures 11 is fed onto the exterior surface of forming structure 50 such that its surface 14 contacts the forming structure, while its surface 17 is oriented toward fluid nozzle 90. Accordingly, the small cusps 13 of the apertures 11 are oriented toward nozzle 90.

The effect produced by fluid nozzle 90 on the web of plastic film 10 as it passes therebeneath is generally illustrated in the greatly enlarged cross-section shown in FIG. 1D. In particular, the web 10 has been caused to assume the macroscopic cross-section exhibited by the forming structure 50 without destroying the fine-scale apertures 11. As will be appreciated by those skilled in the art, characteristics inherent in the incoming web or characteristics introduced in earlier phases of the present multi-phase forming process are generally preserved whenever the latter phases of the forming operation are carried out while the web is in a solid rather than a molten state. As a result, the web exhibits a multiplicity of capillary networks 12, each having interconnected sidewalls 12a corresponding to the edges of apertures 56 in forming structure 50. The capillary networks 12 are also ruptured to form apertures 12b in the shape of the apertures 56 in the forming structure. As can be seen from the greatly enlarged fragmentary perspective of FIG. 4, the forming structure 50 exhibits a fiber-like cross-section of the type generally disclosed in commonly assigned U.S. Pat. No. 4,342,314 issued to Radel et al. on Aug. 3, 1982 and incorporated herein by reference. Accordingly, the macroscopically expanded, three-dimensional, apertured web 10 exhibits a similar cross-section.

After completion of the second passing phase the macroscopically expanded, three-dimensional, apertured polymeric web 10 is removed from forming structure 50 and wrapped about idler rolls 110 and 120 from whence it may be fed either to a rewinding station for temporary storage or directly to converting lines where it may be applied to making finished product structures, such as disposable absorbent bandages. In most instances the latter approach is particularly desirable, since it minimizes the loss of caliper which sometimes results when macroscopically expanded, three-dimensional, polymeric webs are rewound under tension.

As will be apparent from the greatly enlarged web cross-section shown in FIG. 1E, the fully processed plastic web of film 10 exhibits a macroscopic cross-section generally similar to that shown in the aforementioned commonly assigned U.S. Pat. No. 4,342,314 to Radel et al. However, web 10 additionally exhibits a fine-scale pattern of apertures 11. As can be observed in FIG. 1E, each of the fine-scale apertures 11 actually forms a small capillary network resembling a tiny volcano, the outermost edges of which end in silky feeling cusps 13. Because the entire surface of the web is subjected to fine scale aperturing on first forming structure 15 prior to undergoing macroscopic expansion and large scale aperturing on forming structure 50, these tiny apertures 11 are present both in the non-debossed land areas of the film as well as in the capillary sidewalls 12a of the capillary networks 12. Due to the tactile impression imparted to the web by cusps 13, web 10 is normally perceived as well suited for sustained contact with the skin. Furthermore, because of the great disparity in cross-sectional size between the capillary networks 12 and the small apertures 11, films of the type generally illustrated in FIG. 1E are also capable of exhibiting excellent fluid handling and skin dryness benefits, i.e., large volumes of fluid deposited on surface 17 are rapidly transferred to surface 14 of the web by virtue of the relatively large cross-section of capillary networks 12, while capillary driven skin drying benefits are provided via the small scale apertures 11 present in the non-debossed land areas which normally contact the wearer's skin in use. In addition, it is believed that the upward projections associated with the tiny apertures 11 act as a network of baffles during gush flow situations, i.e., the large quantities of liquid deposited on surface 17 are caused to flow in many different directions before reaching an edge of the absorbent structure, thereby increasing the probability that the liquid will enter one or more capillary networks 12 before reaching an edge of the absorbent structure. This, in turn, reduces leakage from the edges of the absorbent bandage.

Figure 5A:
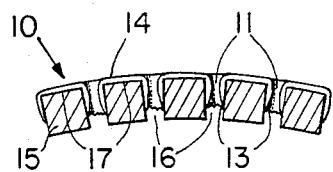
FIG. 5A is a greatly enlarged inset showing the condition of the polymeric web after it has been subjected to a first fluid pressure differential identical to the one illustrated in FIG. 1.
Figure 5B:
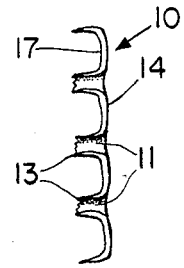
FIG. 5B is a greatly enlarged inset showing the condition of the plastic web after its removal from the first forming structure illustrated in FIG. 1.
Figure 5:
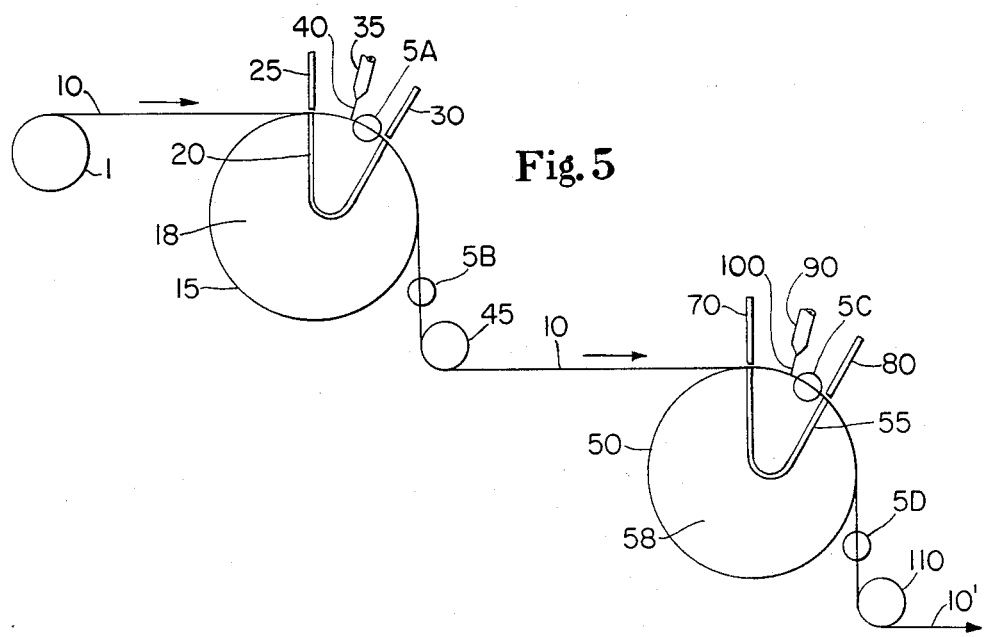
FIG. 5 is a simplified schematic illustration of an alternative two-phase forming process of the present invention.

FIG. 5 is a simplified illustration of an alternative multi-phase polymeric web forming process of the present invention. Like the process generally illustrated in FIG. 1, the process shown in FIG. 5 is carried out in two discrete phases. As can be seen from a comparison of FIGS. 5A and 5B to FIGS. 1B and 1C, respectively, the first phase of the process which provides the fine-scale apertures 11 in the web of film 10 is essentially identical. However, in the embodiment shown in FIG. 5, the film is fed directly onto a second forming structure 50, identical to the one shown in FIG. 1, without reverse wrapping of the film. Accordingly, surface 17 is placed in contact with forming structure 50, while surface 14 is placed so that it will be contacted by the liquid jet 100 issuing from fluid nozzle 90.

With the exception of reversing the position of stationary baffles 70 and 80 and reversing the direction of rotation of forming structure 50 about forming drum 58, the second phase of the process shown in FIG. 5 is substantially identical with that shown in FIG. 1. The cross-section which results after passage of the web of film under fluid nozzle 90 is generally shown at 10' in FIG. 5C. As with the embodiment of FIG. 1, the web of film 10' has been caused to assume the macroscopic, three-dimensional cross-section of forming structure 50 and has been apertured in those areas coinciding with apertures 56 in the forming structure. The capillary networks 12' thus formed are generally similar to the capillary networks 12 shown in web 10 of FIG. 1 with the exception that the cusps 13 of the small apertures 11 are oriented toward rather than away from the forming structure 50.

After passing beyond stationary baffle 80, the macroscopically expanded, three-dimensional, apertured web of film 10' is passed about idler roll 110 and fed either to suitable rewind apparatus for temporary storage or directly to a converting operation for incorporation into the final product in which the web is to be employed.

The final cross-section of the resultant web 10' is shown after removal from forming structure 50 in the greatly enlarged inset of FIG. 5D. While the web of film 10' offers many of the same performance attributes relative to fluid handling as the web of film 10 shown in FIG. 1E, it exhibits a different tactile response, particularly when one touches the non-debossed land areas of the web. This is because of the difference in orientation of the cusps 13 of the fine scale apertures 11 located substantially throughout the macroscopic cross-section of the web.

As will be appreciated by those skilled in the art, process embodiments of the present invention which utilize multiple forming structures offer considerable flexibility with respect to the types of characteristics which may be provided in a single, macroscopically expanded, three-dimensional, apertured plastic web. In addition, they permit the production of macroscopically expanded webs exhibiting a substantially uniform macroscopic cross-section not only across the non-debossed land areas of the web's cross-sectional profile, but also along the sidewalls of the capillary networks formed in the web as it undergoes macroscopic expansion.

Notwithstanding the advantages afforded by the use of multiple forming structures in carrying out the present multi-phase web forming process, there may be circumstances when it is particularly desirable to practice the present invention using only a single three-dimensional forming structure. These situations may involve the production of polymeric webs wherein it is desired to provide macroscopic expansion to form relatively large capillary networks in combination with fine-scale aperturing of the web only in the non-debossed land areas of the web, i.e., the sidewalls of the capillary networks would remain substantially imperforate. It may also in certain instances be desirable to provide macroscopic conformance of a plastic web to the three-dimensional cross-section of the forming structure with only fine-scale aperturing rather than large scale aperturing in the end walls of the capillary networks formed in the web. In still other situations, it may be desirable to provide fine scale aperturing in the end walls of the capillary networks in conjunction with fine scale aperturing in the non-debossed land areas of the web without fine-scale aperturing in the sidewalls of the capillary networks. The multi-phase process embodiments illustrated in FIGS. 6, 8, 9 and 10 are illustrative of multi-phase forming processes of the present invention which are carried out utilizing only a single forming structure containing not only the desired macroscopic cross-sectional profile, but also the desired fine-scale aperturing pattern.

Figure 6:
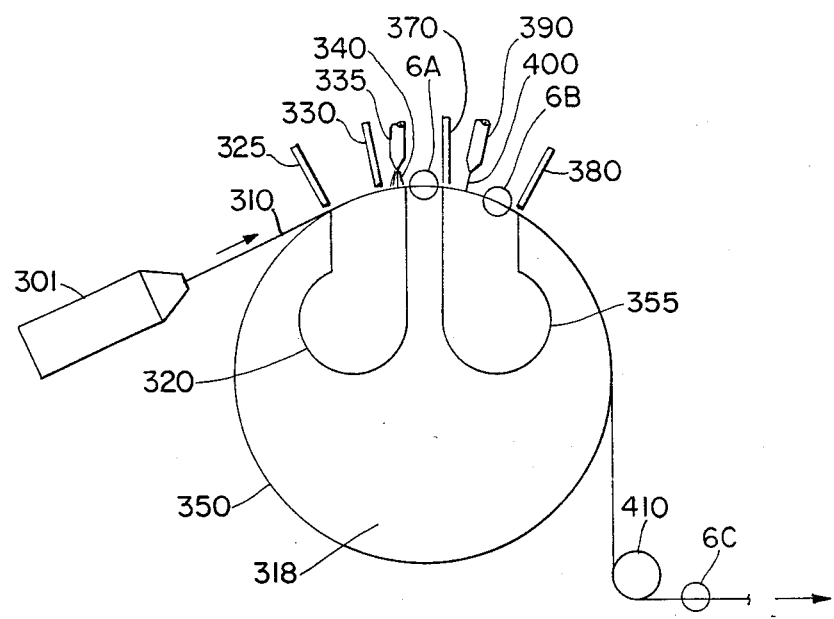
FIG. 6 is a simplified schematic illustration of an alternative two-phase forming process of the present invention.
Figure 7:
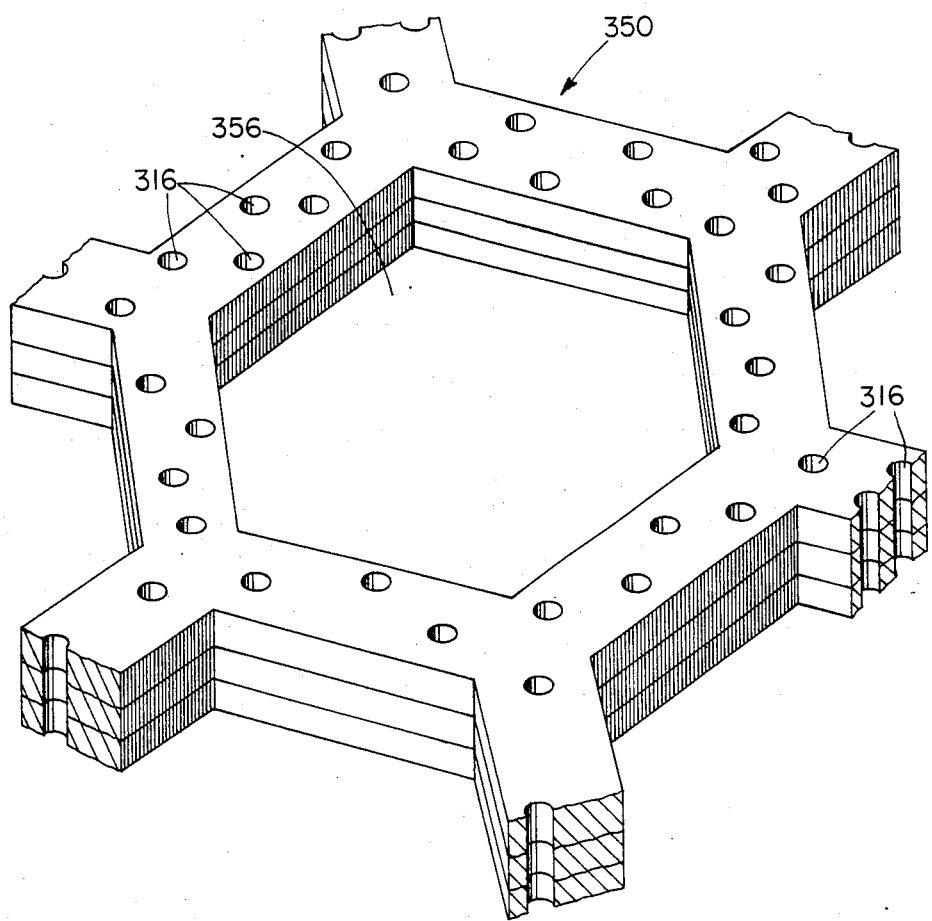
FIG. 7 is a greatly enlarged fragmentary view of the forming structure utilized to carry out the two-phase process generally disclosed in FIG. 6.

FIG. 6 is a simplified schematic illustration of one such process of the present invention. The single three-dimensional forming structure 350 utilized on forming drum 318, which is generally similar to forming drums 18 and 58 of FIG. 1, is shown in the greatly enlarged, fragmentary perspective view of FIG. 7. The macroscopic cross-sectional profile of forming structure 350 is generally similar to that of forming structure 50 shown in FIG. 4. Macroscopic cross-section apertures 356 correspond generally to macroscopic cross-section apertures 56 of the forming structure 50 shown in FIG. 4. However, forming structure 350 also includes a multiplicity of much smaller apertures 316 extending from the film contacting to the non-film contacting surface of the forming structure. These apertures 316 are of the same general size range as the apertures 16 in forming structure 15 shown in FIG. 2. If the forming structure 350 is made utilizing the laminar construction techniques generally disclosed in commonly assigned U.S. Pat. No. 4,508,256 issued to Radel and Thompson on Apr. 2, 1985 and incorporated herein by reference, these relatively small apertures 316 may be provided by etching each of the lamina utilized to make the composite forming structure 350 prior to final assembly. Alternatively, if the apertures 316 are extremely small in size, it may be desirable to form a laminate forming structure 50 in the manner generally disclosed in the aforementioned commonly assigned U.S. Patent to Radel et al. and thereafter utilize laser drilling techniques to add the desired pattern of small apertures 316 to form the structure 350. This avoids filling of the small apertures 316 by the copper plating used to bond the various lamina to one another during the furnace brazing operation, as generally taught in the aforementioned patent to Radel et al.

The multi-phase polymeric web forming process generally illustrated in FIG. 6 is particularly desirable in those circumstances where it is desired to provide a relatively large overall caliper in the resultant plastic web, as well as good replication of the macroscopic, three-dimensional cross-section of the forming structure. Deep drawing of the film is generally best carried out while the film is at an elevated temperature and subject to a sustained fluid pressure differential such as vacuum. In the embodiment disclosed in FIG. 6, this is preferably accomplished by mounting a conventional extruder 301, similar to extruder 101 in FIG. 1, such that a continuous web of thermoplastic resin 310, similar to web of resin 10 in FIG. 1A, is extruded at a temperature above the melt temperature directly onto the surface of forming structure 350. Since it is preferable to maintain the temperature of the web in an elevated condition to maximize conformance when using vacuum as the fluid pressure differential, no chill rolls are used on the FIG. 6 embodiment. It is of course recognized that the incoming web may also be fed from a supply roll similar to that shown in FIG. 1. However, in the latter case it is generally preferred that the temperature of the incoming film be elevated sufficiently to soften it and make it more conformable. When using roll stock this is typically accomplished by applying hot air or steam to the film prior to subjecting it to vacuum forming.

In the embodiment shown in FIG. 6 the web of relatively soft resin 310 passes beneath a first stationary baffle 325 and is immediately subjected to a fluid pressure differential via vacuum chamber 320 located in fixed position at the interior of forming drum 318. If desired, hot air jets (not shown) may be mounted opposite vacuum chamber 320 to assist in causing the molten resin 310 to macroscopically conform to the cross-section of forming structure 350 and to rupture to form apertures substantially coinciding with the macroscopic cross-section apertures 356 in the forming structure 350.

In order to assist in cooling the soft web of resin while it is at maximum caliper, a second stationary baffle 330 and a cooling liquid nozzle 335 are preferably used to apply a low-pressure, e.g., typically below about 50 psig, spray of cooling liquid 340 to the deeply drawn web 310 prior to its leaving the influence of vacuum chamber 320. The baffle 330 helps to prevent the cooling liquid 340 from reaching the vacuum forming zone, as this could adversely impact upon the macroscopic web conforming and aperturing operation. While this liquid cooling step is not generally critical at relatively low production speeds, i.e., speeds less than about 50 feet per minute, it has been found that as the web production speed, and hence the speed of the forming structure 350, increases, adequate cooling of the film may not occur before the film leaves the influence of the forming vacuum. This can result in spring-back and loss of caliper in the web along with possible closing of some of the macroscopic cross-section apertures formed in the web. Applying cooling liquid 340 while the web is still subject to the influence of the forming vacuum helps to more completely cool the film while it is still subject to the forming vacuum, thereby avoiding the spring-back, loss of caliper and reclosing of holes which may otherwise occur.

More specific details of the aforementioned liquid assisted cooling process are generally disclosed in the commonly assigned copending U.S. patent application of Thurman J. Koger, II, Theodore E. Farrington, Jr. and Eugene Weinshenker entitled PROCESS FOR HIGH-SPEED PRODUCTION OF WEBS OF DEBOSSED AND PERFORATED THERMOPLASTIC FILM, Ser. No. 549,525 filed Nov. 4, 1983, issued on Nov. 12, 1985 as U.S. Pat. No. 4,552,709 and hereby incorporated herein by reference.

Following the liquid assisted cooling operation, the macroscopic cross-section of the web 310 is generally as shown in the greatly enlarged inset of FIG. 6A. The web 310 has been macroscopically conformed to the three-dimensional cross-section of forming structure 350 and capillary networks 312 corresponding to macroscopic cross-section apertures 356 in the forming structure have been formed. The sidewalls of the capillary networks 312a correspond to the sidewalls of the macroscopic cross-section apertures 356 in the forming structure 350, and the apertures 312b in the end walls of the capillary networks 312 correspond substantially in cross-section to the cross-section of the apertures 356 in forming structure 350.

As can be observed from FIG. 6A, the relatively small apertures 316 in forming structure 350 do not significantly impact upon the web 310 when the web is subjected to suction via vacuum chamber 320. This is due to the fact that once the web 310 has been apertured in those areas coinciding with macroscopic cross-section apertures 356, there is normally insufficient fluid pressure differential remaining on opposite sides of the web to cause conformance and aperturing of the web in those areas corresponding to the relatively fine-scale apertures 316 in forming structure 350.

Accordingly, the fine scale apertures corresponding to apertures 316 in forming structure 350 are preferably produced intermediate a pair of stationary baffles 370, 380 by means of a high pressure liquid nozzle 390 which discharges a liquid jet 400 against the exposed surface 314 of the web, as generally shown in FIG. 6. The high pressure liquid jet 400, which is substantially the same as the high pressure liquid jet 40 employed in the process embodiment shown in FIG. 1, causes the macroscopically expanded web 310 to conform and rupture in those areas corresponding to apertures 316 in the forming structure 350. As with the earlier described embodiments employing liquid as either a forming or a cooling assist media, a secondary fixed position vacuum chamber 355 located generally opposite the liquid nozzle 390 captures the liquid 400 which passes through both capillary networks 312 and fine scale apertures 311 in the plastic web 310 and recycles it to one or more pumps (not shown) prior to its return to the nozzle from which it issued. This high pressure liquid jetting operation not only completes the processing operation by providing fine scale aperturing of the web in its non-debossed land areas, but reinforces conformance of the web to the macroscopic cross-section of the forming structure and completely apertures any of the unapertured portions of the web corresponding to apertures 356 in the forming structure.

The cross-section of the finished web is shown in the greatly enlarged inset of FIG. 6C. The web 310 is somewhat similar to the web 10' shown in FIG. 5D. However, there is one principal difference, namely, the sidewalls 312a of capillary networks 312 are substantially unapertured.

Following the fine scale aperturing operation, the completed web passes about idler roll 410 from whence it may be forwarded either to suitable rewinding apparatus for temporary storage or directly to converting operations for incorporation into products employing the plastic web thus produced.

Figure 8:
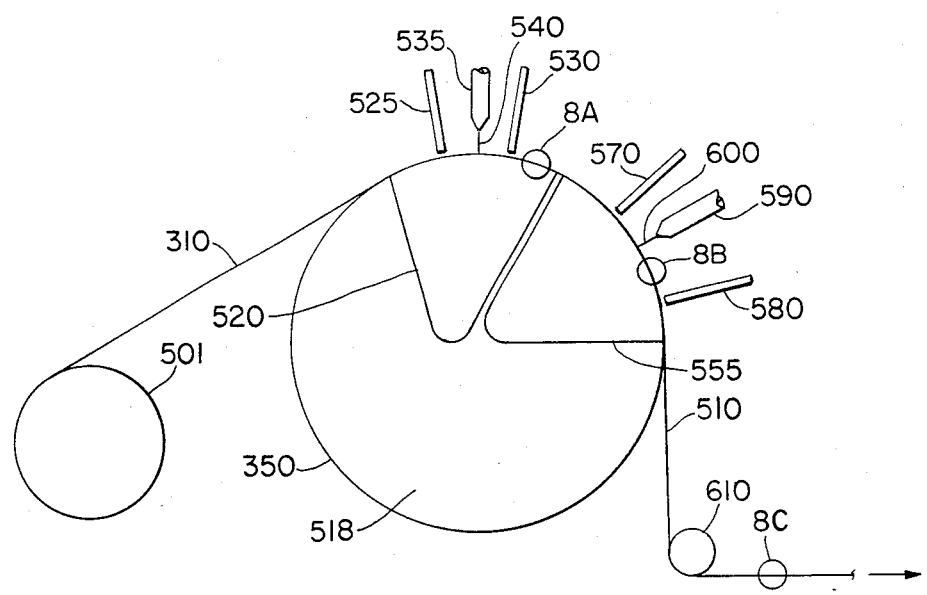
FIG. 8 is a simplified schematic illustration of another two-phase forming process of the present invention.

In FIG. 8 there is shown still another embodiment of the present multi-phase web processing invention wherein a single forming structure is utilized to provide macroscopic expansion/macroscopic aperturing of a plastic web as well as fine scale aperturing of the non-debossed land areas of the web. In the embodiment shown in FIG. 8, a forming structure 350 identical to that employed in the process of FIG. 6 operates about forming drum 518, which is generally similar to forming drum 318. A pair of stationary vacuum chambers 520 and 555 are located adjacent one another at the interior of the forming drum. In the embodiment shown in FIG. 8, a web of plastic 310 is fed in a substantially planar condition from a supply roll 501 onto the surface of forming structure 350. Located intermediate a pair of stationary baffles 525, 530 is a liquid jet nozzle 535 which discharges a high pressure liquid jet 540 against the exposed surface of the web 310. As can be seen from the cross-section of FIG. 8A, the high pressure liquid jet 540 causes macroscopic conformance of the web, thereafter designated as 310' to avoid confusion with the web processed in accordance with the process shown in FIG. 6, as well as aperturing of those portions of the web coinciding with the macroscopic cross-section apertures 356 in forming structure 350. After this phase, the web 310' exhibits a multiplicity of capillary networks 312', each having interconnected, non-apertured side walls 312a' ending to form apertures 312b' corresponding to macroscopic cross-section apertures 356 in forming structure 350. Thus the web cross-section 310' shown in FIG. 8A is generally similar in shape to the web cross-section 310 shown in FIG. 6A. However, the overall length of capillary networks 312', is generally not as great as when vacuum forming is utilized, nor is the image of the forming structure 350 quite as sharp as when the high temperature vacuum forming approach generally illustrated in FIG. 6 is employed.

Figure 17:
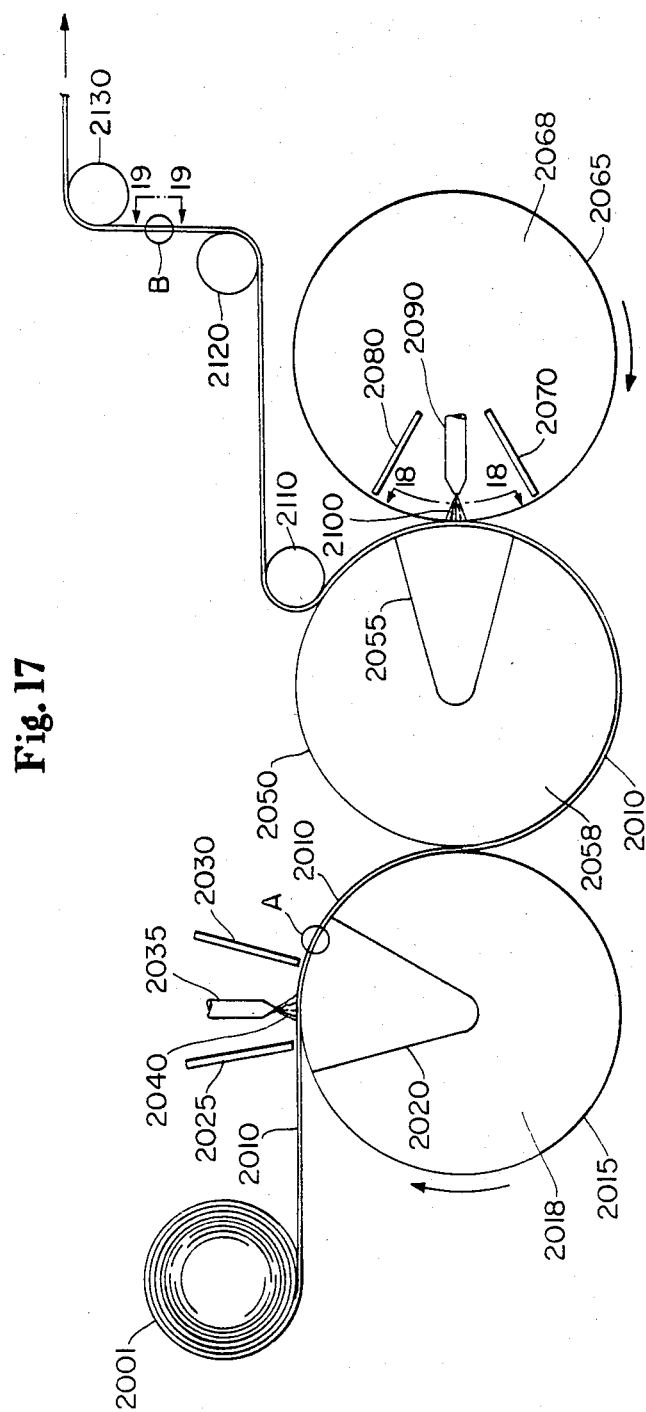
FIG. 17 is a simplified schematic illustration of another two-phase, registered pattern forming process of the present invention wherein a masking element is also employed to produce a polymeric web exhibiting discrete predetermined areas of macroscopic, three-dimensional expansion.

For purposes of macroscopically conforming substantially planar webs of the type herein described to the macroscopic, three-dimensional cross-section of a forming structure, the high pressure liquid jet nozzle, such as nozzle 90 in FIG. 1, nozzle 540 in FIG. 8 and nozzle 2090 in FIG. 17 is typically operated at a pressure in the range of about 400 psig to about 800 psig and a water flow rate in the range of about 8 gallons per minute to about 14 gallons per minute per cross-machine direction inch of width of the plastic web. By way of contrast, when the principal object is to provide fine scale aperturing of the web rather than macroscopic conformation, the high pressure liquid jet nozzle, such as nozzle 35 in FIG. 1, nozzle 390 in FIG. 6, nozzle 590 in FIG. 8, nozzle 790 in FIGS. 9 and 10, and nozzle 2035 in FIG. 17, is typically operated at a pressure in the range of about 800 psig to about 1,200 psig and water flow rates on the order of about 8 gallons to about 14 gallons per minute per cross-machine direction inch of web width.

As can be seen in FIG. 8, high pressure liquid jet nozzle 590 positioned between stationary baffles 570 and 580 discharges liquid jet 600 against the exposed surface 314' of the macroscopically expanded web 310' as it passes therebeneath. The effect of the high pressure liquid jet 600 upon the macroscopically expanded web 310' is substantially identical to that of high pressure liquid jet 400 shown in FIG. 6, i.e., fine scale apertures 311' are created in those areas coinciding with fine scale apertures 316 in forming structure 350. Small cusps 313' are formed on surface 317' of the web about the periphery of each of the fine scale apertures 311'. Thus, with the possible exceptions of slightly less overall caliper and somewhat less accurate replication of the forming structure 350, the resultant web 310' shown in FIG. 8B is identical to web 310 shown in FIG. 6B. As with the embodiment of FIG. 6, water passing through the web from the liquid nozzles is collected in vacuum chambers 520 and 555 and is preferably recycled to one or more pumps which return the liquid to the nozzles from which it issued.

After passing beyond the influence of high pressure liquid jet 600, the resultant web 310' is removed from forming structure 350 about idler roll 610 in the condition generally illustrated in FIG. 8C and is thereafter rewound or fed directly to subsequent converting operations.

It is of course recognized that drying macroscopically expanded, three-dimensional, apertured polymeric webs of the present invention to remove moisture left on its surface by the water assisted cooling and/or jetting operations described herein may be desirable, particularly in the event it is intended to rewind the web for temporary storage prior to undertaking converting operations. This may be accomplished by many and varied web drying techniques well known in the art, e.g., blow drying with hot air, wrapping the web about a multiplicity of rolls which apply centrifugal forces to sling the water from the web, etc. A particularly preferred drying approach which subjects the moving web to ultrasonic vibration is disclosed in the aforementioned commonly assigned, co-pending U.S. patent application of Curro et al., Ser. No. 580,911, which is incorporated herein by reference.

Figure 9:
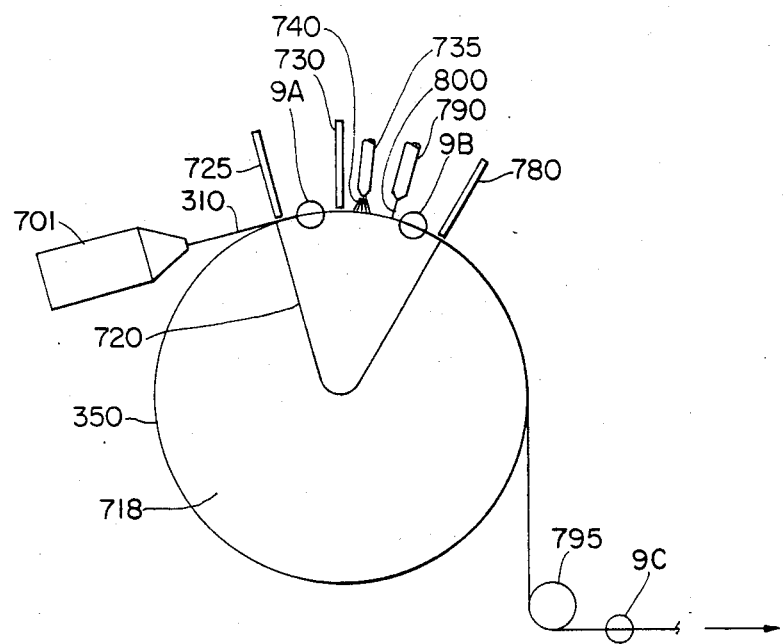
FIG. 9 is a simplified schematic illustration of still another embodiment of a two-phase forming process of the present invention.

FIG. 9 discloses still another embodiment of the present invention which utilizes only a single three-dimensional forming structure. The process shown in FIG. 9 employs a forming structure 350 generally similar to that shown in FIGS. 6 and 8. The forming structure 350 rotates about forming drum 718, generally similar to forming drum 318. Forming drum 718 includes a single, internally located, stationary vacuum chamber 720.

The forming structure 350 is preferably fed by means of an extruder 701 which supplies a web of molten resin 310 directly onto its surface. A first stationary baffle 725 is aligned substantially even with the leading edge of vacuum chamber 720. The relatively high temperature of the web of soft resin 310 aids the web in conforming to the macroscopic cross-section of forming structure 350 under the influence of suction from vacuum chamber 720 in a manner substantially identical to that disclosed in connection with the first phase of the process disclosed in FIG. 6. Thus the cross-section of web 310 upon aperturing of those portions of the web coinciding with apertures 356 in the forming structure is generally as shown in FIG. 9A, which is substantially identical to that of the web 310 shown in FIG. 6B.

In order to avoid spring-back of the web along with possible loss of caliper and closing of some of the apertures corresponding to apertures 356 in the forming structure, the web embodiment 310 shown in FIG. 9 is preferably cooled while still subject to the forming vacuum provided in chamber 720. Since it is generally desirable to reduce the temperture of the macroscopically expanded web to its solid state temperature prior to subjecting it to high pressure liquid jetting to avoid damage, a low pressure liquid spray 740 is preferably applied to the web adjacent stationary baffle 730 by means of a low pressure liquid nozzle 735. As pointed out earlier herein, the need for such liquid-assisted cooling generally increases as the web production speed increases beyond about 50 feet per minute.

Figure 9B:
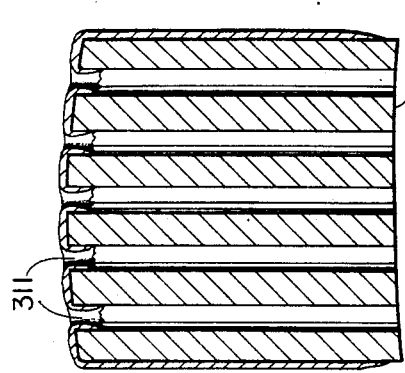
FIG. 9B is greatly enlarged inset showing the condition of the web after it has been subjected to a second fluid pressure differential comprising a high pressure liquid jet which serves to aperture the web in those areas corresponding to the small apertures in the land areas of the forming structure and to further cool the web before it leaves the influence of the forming vacuum.

Fine scale aperturing and further cooling of the web are provided via high pressure liquid nozzle 790 located intermediate stationary baffles 730 and 780. The high pressure liquid jet nozzle 790 discharges a liquid jet 800 onto the exposed surface of the macroscopically conformed web 310. The liquid jet 800 creates apertures 311 corresponding to the small apertures 316 in the forming structure, as generally illustrated in FIG. 9B, which is substantially identical to the cross-section shown in FIG. 6B. In a preferred embodiment, the temperature of the liquid jet 800 is sufficiently low that it aids in further cooling the web 310, thereby better preserving the macroscopic cross-section imparted to the film by the suction emanating from within vacuum chamber 720.

Figure 9C:
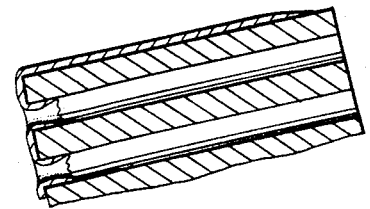
FIG. 9C is a greatly enlarged inset showing the resultant web after the two-phase forming process generally illustrated in FIG. 9 has been completed.
Figure 9C:
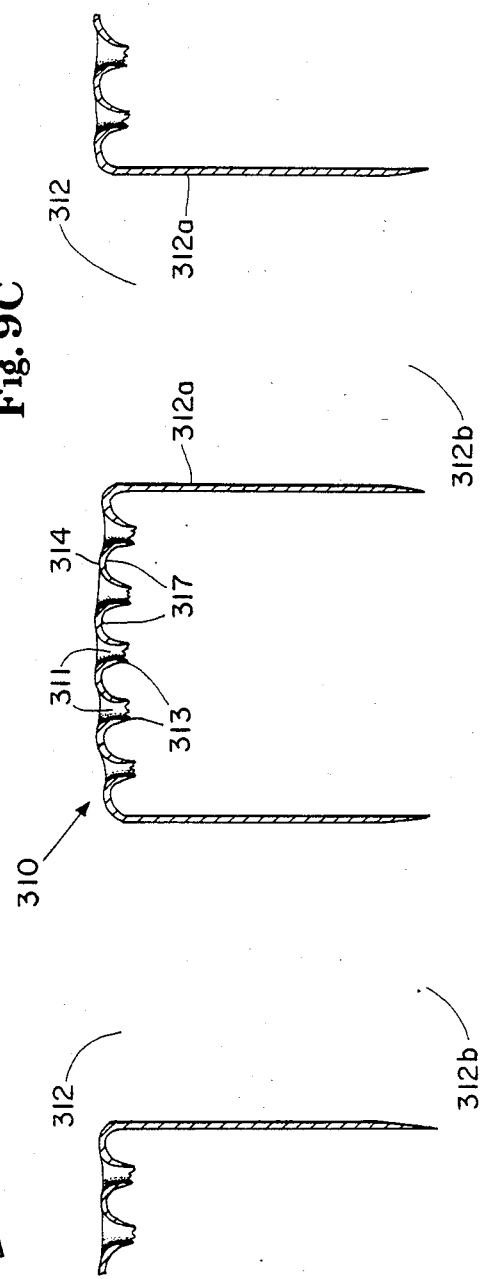

Thus, the process embodiment of FIG. 9 functions in a manner generally similar to that of FIG. 6 utilizing a slightly different apparatus configuration, the chief difference involving the use of a single vacuum chamber 720 spanning both forming phases. The resultant web 310 shown in greatly enlarged cross-section in the inset of FIG. 9C is substantially identical to the web shown in FIG. 6C.

As with the earlier embodiments of the present invention, the web 310 is fed about an idler roll 795 and thereafter directed either to suitable rewind apparatus or to a converting operation.

Figure 10:
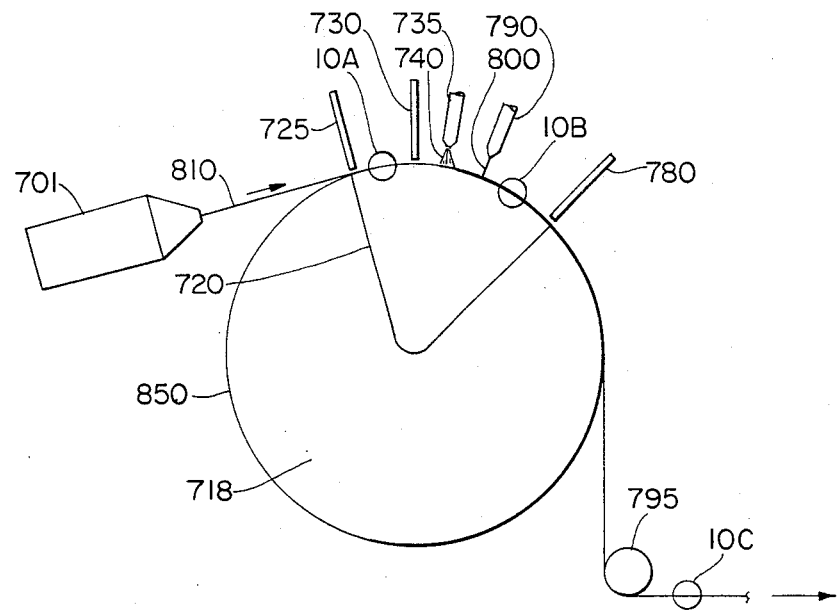
FIG. 10 is a simplified schematic illustration of a process generally similar to that shown in FIG. 9 with the principal exception that a different forming structure is employed.

The process embodiment shown in FIG. 10 is substantially identical to the process embodiment shown in FIG. 9 with one major exception, the configuration of the forming structure. In particular, the forming structure 850 utilized in the embodiment of FIG. 10 is shown in greatly enlarged fragmentary perspective in FIG. 11. The forming structure 850 exhibits an overall cross-sectional pattern similar to that of forming structure 50 shown in FIG. 4, including a multiplicity of macroscopic cross-section apertures 856 which are generally similar to apertures 56 in forming structure 50. However the base of the apertures 856 is closed by means of a perforate wall 857. This perforate wall 857 includes a multiplicity of relatively small apertures 816, as generally shown in FIG. 11.

Figure 11:
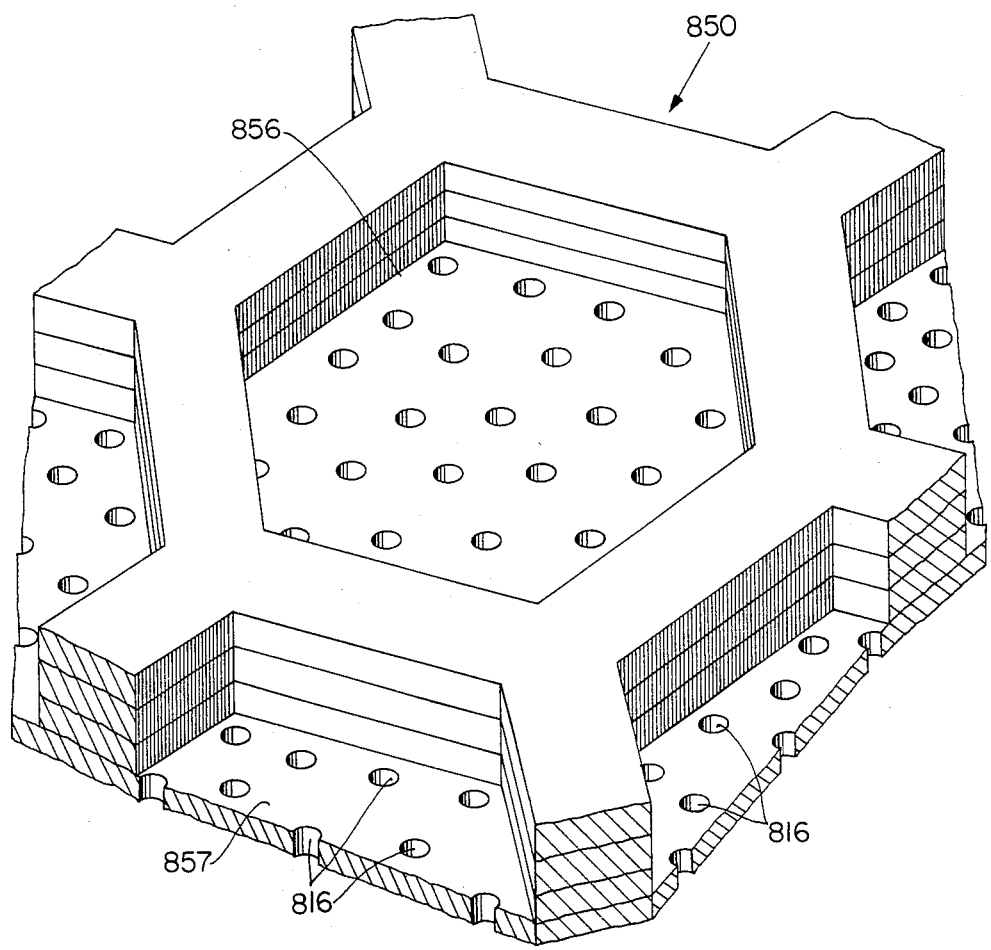
FIG. 11 is a greatly enlarged fragmentary view of the forming structure employed in the process of FIG. 10.

Techniques which may be readily adapted for making forming structures of the type generally disclosed in FIG. 11 are disclosed in commonly assigned U.S. Pat. No. 4,395,215 issued to Bishop on July 26, 1983 and hereby incorporated herein by reference.

Figure 10A:
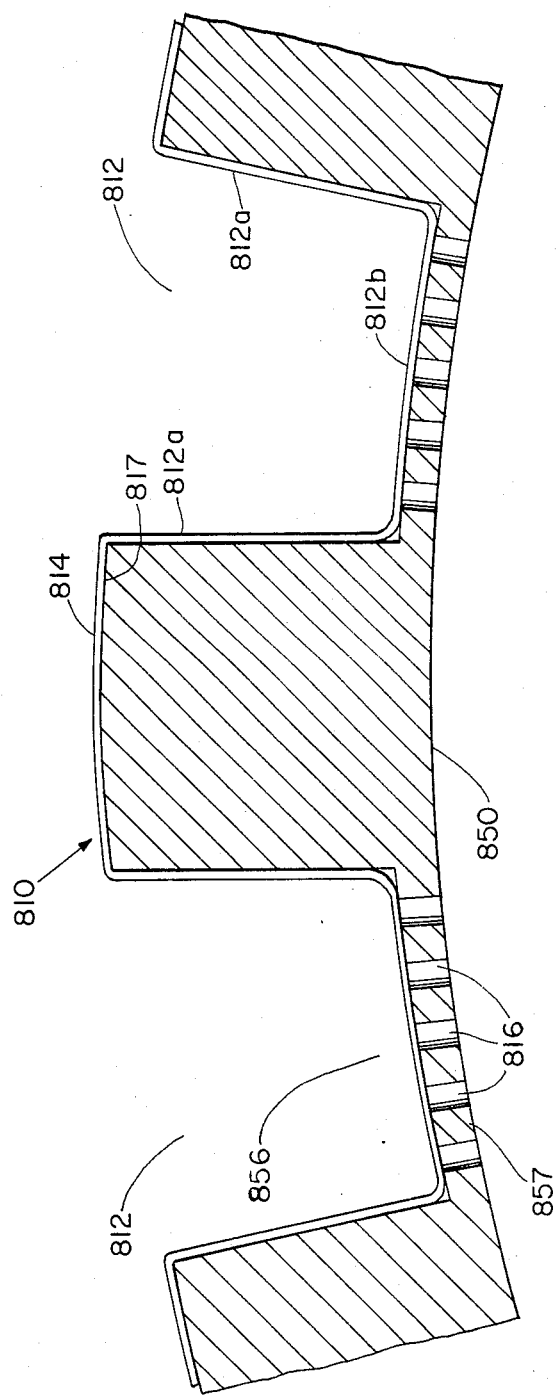
FIG. 10A is a greatly enlarged inset showing the condition of the web after it has been subjected to a first fluid pressure differential comprising suction applied adjacent the innermost surface of the forming structure.

In use, a web of soft heated resin 810 is preferably extruded from extruder 701 onto the surface of forming structure 850, as generally shown in FIG. 10. The influence of suction emanating from within vacuum chamber 720 causes the web 810 to assume the macroscopic profile of the forming structure 850, as generally shown in FIG. 10A. However, because of the relatively small size of apertures 816 in the end wall portions 857 of the forming structure 850, the fluid pressure differential applied by the vacuum chamber 720 is generally not sufficient to cause rupture of the web in those areas coinciding with apertures 816 in the forming structure.

As with the embodiment shown in FIG. 9, a low pressure liquid spray 740 may be applied adjacent stationary baffle 730 by means of a low pressure liquid nozzle 735. Since the web is not apertured at this point, the applied cooling liquid cannot pass directly through the web at the point of application. Accordingly, alternative liquid collection means may be provided adjacent the lateral edges of the web. Preferably cooling nozzle 735 is so repositioned adjacent the periphery of forming drum 718 that the bulk of the applied cooling liquid will drain toward high pressure liquid nozzle 790 by gravity.

To provide small scale aperturing in the end walls of the capillary networks 812, high pressure liquid nozzle 790 issues a jet of liquid 800 against the exposed surface 814 of the macroscopically expanded web 810. As with the embodiment of FIG. 9, the high pressure liquid jet 800 apertures the web 810 in those areas which are as yet unapertured, in this case those areas coinciding with apertures 816 in the forming structure. In addition, the liquid jet 800 preferably further assists in further cooling the web 810 in its fully conformed and maximally distended condition, since it is at this point still subject to the forming vacuum.

As a result, the finished web 810 passing from the forming structure 850 exhibits the cross-section generally shown in the greatly enlarged inset of FIG. 10C. Each capillary network 812 is formed by substantially continuous, interconnected, imperforate sidewalls 812a. Each capillary network 812 also includes an end wall portion 812b which contains a multiplicity of relatively small apertures 811 corresponding to apertures 816 in forming structure 850. As described earlier herein, the apertures 811 form small capillary networks, each resembling a volcano having small cusps 813 about its periphery on surface 817 of the web.

Macroscopically expanded, three-dimensional, apertured polymeric webs of the type generally disclosed in FIG. 10C are believed particularly well suited for use in those situations where it is desired to isolate the wearer's skin from a moist absorbent member adjacent the lowermost surface 817 of the web, yet provide vapor permeability through the small apertures 811 provided in the end walls 857 of the capillary networks 812.

Figure 12:
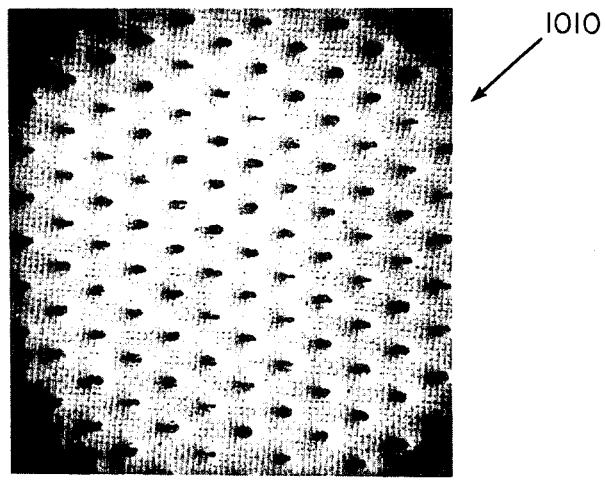
FIG. 12 is a plan view photograph, enlarged many times actual size, of a macroscopically expanded, three-dimensional, apertured polymeric web made using a two-phase forming process generally similar to that disclosed in FIG. 1.

FIG. 12 is a plan view photograph, enlarged many times actual size, of a macroscopically expanded, three-dimensional, apertured plastic web made via a process of the type generally disclosed in FIG. 1, but exhibiting a different macroscopic, three-dimensional pattern.

The web 1010 shown in FIG. 12 was formed from 1 mil thick polyethylene which was first apertured on a fine scale mesh screen comprised of wire monofilaments having a diameter of about 3.7 mils and a mesh count of 120 filaments by 120 filaments per square inch. The finely apertured web was thereafter reverse wrapped onto a macroscopic forming structure of the type generally similar to that disclosed in FIG. 4, but exhibiting a different macroscopic, three-dimensional pattern. The macroscopic forming structure exhibited an overall thickness of 16 mils and a regularly spaced pattern of substantially round apertures, each measuring approximately 26 mils at its point of maximum width, said apertures being spaced approximately 67 mils from one another, center-to-center distance. The web was formed using a two-phase forming process of the type generally disclosed in FIG. 1 by applying a pressure of 1000 psig and a water flow rate of 10 gallons per minute per inch of web width at high pressure liquid nozzle 35 and a pressure of 500 psig and a water flow rate of 8 gallons per minute per inch of web width at high pressure liquid nozzle 90. The vacuum at chamber 20 was maintained at 2 inches of mercury, and the vacuum at chamber 55 was maintained at 2 inches of mercury. The resultant web 1010 exhibited an overall caliper of approximately 20 mils, as measured under no load, and a soft and pleasing tactile impression, particularly in those non-debossed areas coinciding with the land areas of the forming structure.

Figure 13:
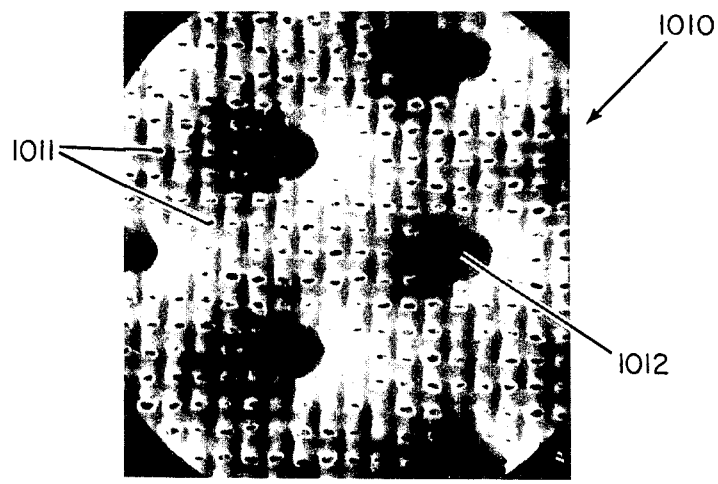
FIG. 13 is another plan view photograph of the web illustrated in FIG. 12, but at a much higher level of magnification.

FIG. 13 is a further enlarged photograph of a section of the web shown generally in FIG. 12. The tiny apertures 1011 the cusps of which are oriented out of the plane of the paper correspond to the void spaces at the interstices formed between the intersecting filaments of the first woven wire forming structure, while the macroscopic cross-section capillary networks 1012, which are oriented into the plane of the paper, correspond to the macroscopic cross-section apertures present in the macroscopic forming structure.

The specific conditions under which macroscopically expanded, three-dimensional web 1010 was produced and the apparatus utilized are more fully described in connection with Example 1, which is described in detail near the end of the present specification.

Figure 14:
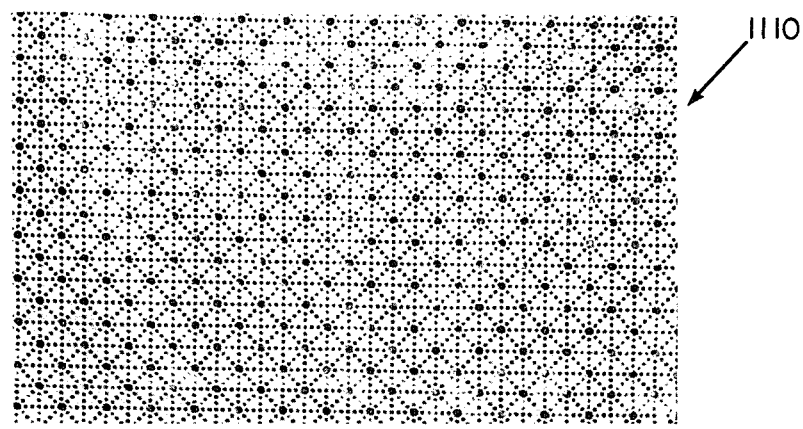
FIG. 14 is a plan view photograph, enlarged many times actual size, of a macroscopically expanded, three-dimensional, apertured polymeric web made using a two-phase forming process generally similar to that disclosed in FIG. 6.

FIG. 14 is a plan view photograph, enlarged many times actual size, of an alternative plastic web made utilizing a multi-phase web forming process generally similar to that disclosed in FIG. 6. This particular web 1110 exhibits fine-scale apertures in combination with macroscopic cross-section capillary networks of several different sizes. As can best be seen in the greatly enlarged segment of FIG. 15, the relatively small apertures 1111 which form tiny volcano-shaped capillary networks correspond to the fine-scale apertures which are present in the land areas of the macroscopic forming structure on which the web was formed, while the macroscopic cross-section capillary networks 1112 and 1115 correspond to the macroscopic cross-section apertures which are also present in the forming structure. The cusps associated with fine-scale apertures 1111 and the capillary networks 1112 and 1115 are all oriented into the plane of the paper.

The specific conditions under which macroscopically expanded, three-dimensional, apertured polymeric web 1110 was produced are more fully described in connection with Example 11, which is described in detail near the end of the present specification.

Figure 16:
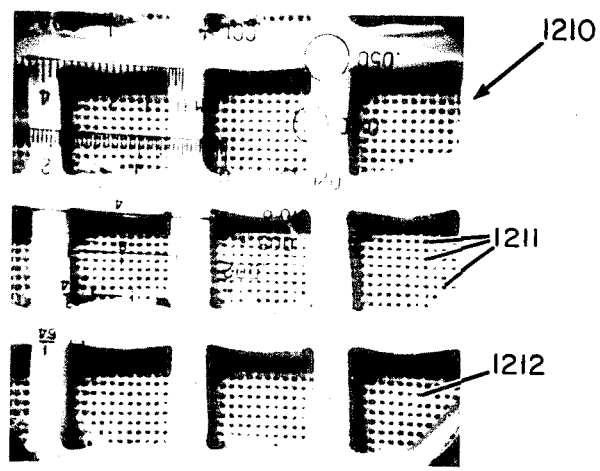
FIG. 16 is a plan view photograph, enlarged many times actual size, of a macroscopically expanded, three-dimensional, apertures polymeric web made utilizing a multi-phase forming process of the present invention and a forming structure generally similar to the one disclosed in FIG. 11.

Finally, FIG. 16 is a plan view photograph of a polymeric web of the type generally disclosed in FIG. 10, enlarged many times actual size.

The web 1210 was processed generally in accordance with the multi-phase process schematically shown in FIG. 10. It includes a multiplicity of capillary networks 1212 corresponding to the capillary networks present in the forming structure. The apertures 1211 located in the end walls of the capillary networks correspond to small apertures located in the end walls of the capillary networks contained in the forming structure.

The specific conditions under which web 1210 was produced are more fully described in connection with Example 111, which is also described in detail near the end of the present specification.

As will be appreciated, it is not necessary that the entire surface of a polymeric web be processed in accordance with the present invention. It may, for example, be desirable to provide a pattern of tiny apertures across the entire surface of a web while macroscopically expanding and/or macroscopically aperturing the web only in discrete predetermined areas. One particularly preferred approach for carrying out such a process is disclosed in FIG. 17.

FIG. 17 is yet another simplified schematic illustration of a multi-phase polymeric web forming process of the present invention. Like the process generally illustrated in FIG. 1, the process shown in FIG. 17 is carried out in two discrete phases. Film supply roll 2001 is substantially equivalent to film supply roll 1 in FIG. 1; web 2010 is substantially equivalent to web 10 in FIG. 1; forming drums 2018 and 2058 are substantially equivalent to forming drums 18 and 58, respectively; vacuum chambers 2020 and 2055 are substantially equivalent to vacuum chambers 20 and 55 in FIG. 1; stationary baffles 2025 and 2030 are substantially equivalent to stationary baffles 25 and 30 in FIG. 1; forming structures 2015 and 2010 are substantially equivalent to forming structures 15 and 50 in FIG. 1; and first phase high-pressure nozzle 2035 which applies a high pressure liquid jet 2040 is substantially equivalent to high pressure liquid nozzle 35 which applies a high pressure liquid jet 40 in FIG. 1. However, the process system illustrated in FIG. 17 employs a nip type transfer between forming structure 2015 and forming structure 2050. This permits transfer of the web 2010 without loss of register between the patterns on forming structures 2015 and 2050. This is possible because the nip transfer avoids machine direction stretching of the web until both phases of the process have been carried out.

The process system illustrated in FIG. 17 differs from that illustrated in FIG. 1 in one principal aspect. In particular, the second phase high pressure liquid nozzle 2090, which is substantially equivalent to high pressure liquid nozzle 90 in FIG. 1, is located inside a third drum 2068 which carries a rotating mask element 2065 about its periphery. As with the embodiment shown in FIG. 1, a pair of stationary baffles 2070 and 2080 enclose high pressure nozzle 2090. However, the latter baffles are located within the drum 2068.

High pressure liquid nozzle 2090 discharges a high pressure liquid jet 2100 substantially equivalent to high pressure liquid jet 100 in FIG. 1. However, the presence of mask element 2065 permits the high pressure liquid jet 2100 to contact web 2010 only in those areas coinciding with the openings in the apertured mask element 2065.

Figure 18:
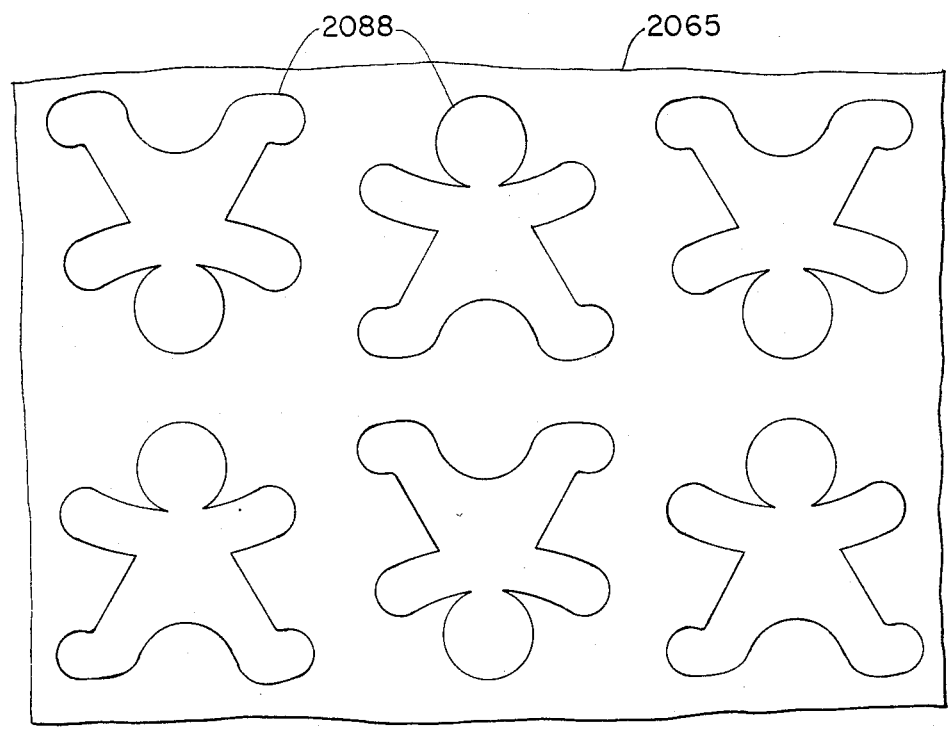
FIG. 18 is a view of the inside of the masking element, taken along view line 18—18 of FIG. 17.

As will be appreciated, the openings in the mask element 2065 can be of any desired shape and may, for example, include a logo or similar decorative pattern which will define the pattern of macroscopic expansion which will be carried out as liquid jet 2100 contacts web 2010 while it is supported on forming structure 2050. An exemplary mask pattern is illustrated in FIG. 18, which is taken along view line 18—18 of FIG. 17. This particular pattern comprises a multiplicity of apertures 2088, each resembling an infant with outstretched arms and legs.

Figure 19:
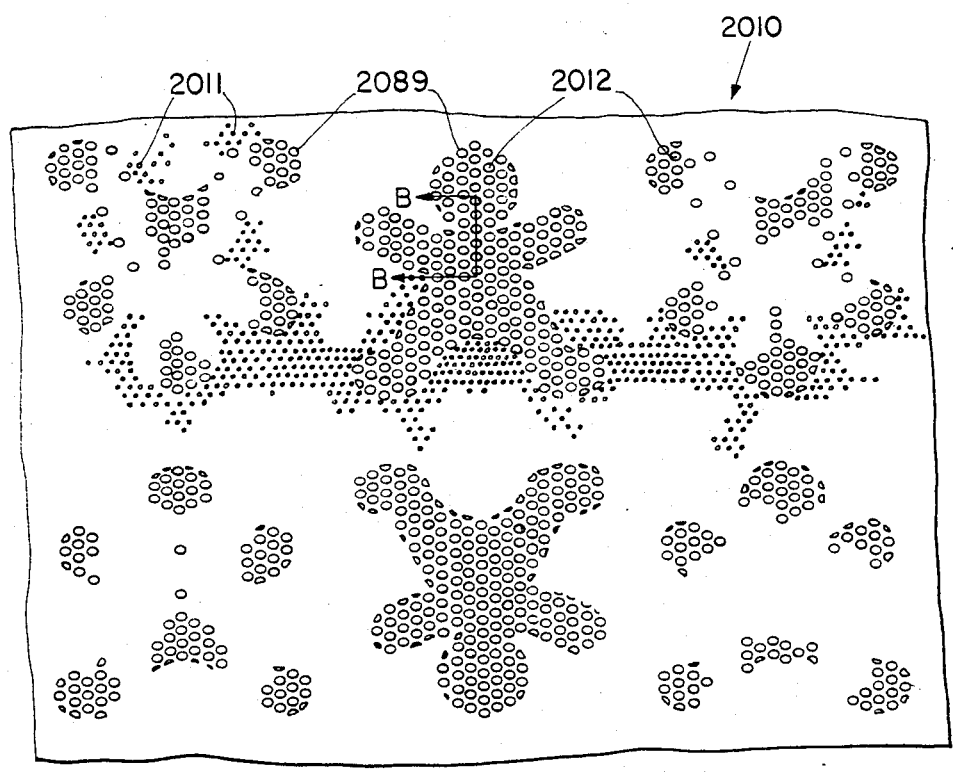
FIG. 19 is a simplified schematic view of the finished web shown in FIG. 17, taken along view line 19—19 of FIG. 17.

As will be appreciated by those skilled in the art, the cross-section of web 2010 after high pressure water jetting by first phase nozzle 2035, if examined at the inset labeled "A" in FIG. 17, will be identical to that of web 10 shown in FIG. 1B. Similarly, the cross-section of that portion of the web 2010 which coincides with the apertures 2088 in mask element 2065, if examined at the inset labeled "B" in FIG. 17, will be substantially identical to that of web 10 in FIG. 1E. However, as will be appreciated from FIG. 19, which is a simplified schematic view taken along view line 19—19 of FIG. 17, those portions of web 2010 which did not align with apertures 2088 in mask element 2065 will exhibit only the finely apertured pattern analogous to that of web 10 in FIG. 1C, while those portions of the web 2089 which coincided with apertures 2088 in masking element 2065 as it passed beneath nozzle 2090 i.e., coinciding with a section line such as "B"—"B" in FIG. 19, will exhibit both the fine-scale apertures 2011 and a multiplicity of capillary networks 2012 which correspond to capillary networks 12 in the web embodiment of FIG. 1. To more clearly differentiate portions 2089 from the balance of the web illustrated in the simplified schematic of FIG. 19, the fine scale apertures 2011 (which are present across the entire surface of the web) are not shown in the simplified schematic of FIG. 19 in those portions of the web 2089 which coincided with apertures 2088 in masking element 2065 as it passed beneath nozzle 2090.

As shown in FIG. 17, the finally processed web embodiment 2010 is preferably removed from forming structure 2050 about a series of idler rolls 2110, 2120 and 2130, from whence it is directed either to suitable rewind apparatus or to on-line converting operations, as desired.

Processing systems of the type generally shown in FIG. 17 are particularly preferred in those situations where it is desirable to hold close register between the pattern on forming structure 2015 and the pattern on forming structure 2050. Furthermore, the use of a mask element, such as 2065, permits the producer to utilize a wider range of liquid jetting pressures to issue from high pressure nozzle 2090 since there is no degradation of any characteristics initially imparted to those portions of the web which do not coincide with apertures 2088 in mask element 2065 as it passes beneath nozzle 2090.

It is recognized that the ability to accurately register patterns between adjacent forming structures makes it possible to produce webs exhibiting a wide range of effects. It is further recognized that because it is possible to adjust the registration of the patterns on adjacent forming structures relative to one another it is feasible to combine the selected patterns with one another to produce many different effects in the resultant web.

It is believed that the description contained herein will enable one skilled in the art to practice the present invention in many and varied forms. Nonetheless, the following exemplary embodiments are set forth for purposes of illustration:

EXAMPLE I

The macroscopically expanded, three-dimensional apertured web 1010 shown in FIGS. 12 and 13 was made in step-wise fashion, generally following the two stages of the process disclosed in FIG. 1. The input web (10) was polyethylene, 0.001 inches thick (Consolidated Thermoplastics, #24765, Harringtgon, Del. 19952). This web (10) was fed onto forming structure (15) at a speed of 500 feet per minute and subjected to the high pressure water jet (40). The water temperature was 165° F., the water pressure about 1000 psig, and the water flow about 10 gallons per minute per cross-machine direction inch of web width. The forming structure was a woven wire 120×120 mesh screen, having 0.0037 inch wires. (Cambridge Wire Cloth Co., Cambridge, Md. 21613.) This first stage produced a web containing a multiplicity of small apertures, approximately 0.004 inches in diameter, at a density of 120 such apertures per linear inch in both directions. This finely apertured web was then wound onto a take-up roll. The second stage was carried out by taping a 6 inch by 12 inch portion of the aforementioned finely apertured web onto a different forming structure. This forming structure contained apertures of approximately 0.026 inch in diameter spaced 0.067 inches center to center on a 60° array. The finely apertured web was reverse wrapped (small capillary networks oriented toward the second high pressure liquid nozzle) on the latter forming structure and subjected to a high pressure water jet at a web speed of approximately 500 feet per minute. The water temperature was 155° F., the water pressure was about 500 psig and the water flow was approximately 8 gallons per minute per cross-machine direction inch of web width. The resultant macroscopically expanded, three-dimensional, apertured web shown in FIGS. 12 and 13 contained small elliptically shaped apertures 1011 measuring approximately 0.004 inches across their major axis and elliptically shaped macroscopic cross-section capillary networks 1012 measuring apprriximately 0.022 inches across their major axis. The overall no load caliper of the expanded web was approximately 0.015 inches.

EXAMPLE II

Figure 15:
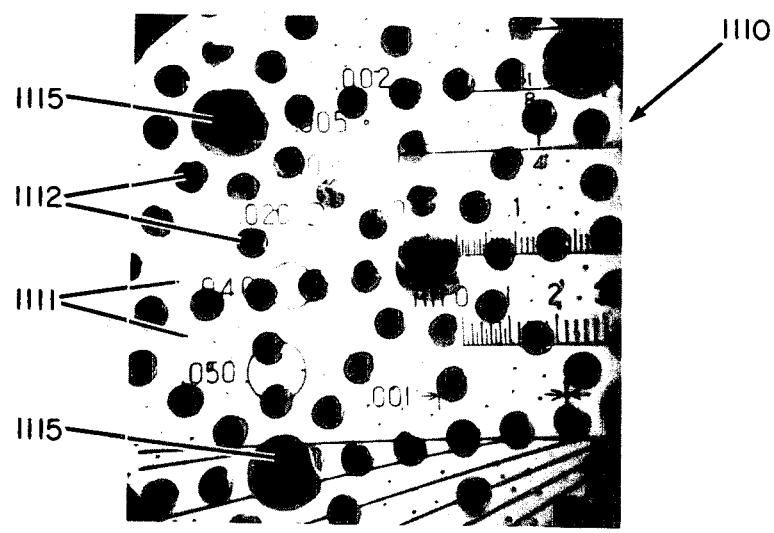
FIG. 15 is another view of the web shown in FIG. 14, but at a much higher level of magnification.

The macroscopically expanded, three-dimensional, apertured polymeric web 1110 shown in FIGS. 14 and 15 was made by the type of process generally disclosed in FIG. 6. A National Rubber Machinery Co. Pacemaker III (NRM Process Systems, P.O. Box 25, Columbiana, Ohio 4408) extruder, with a 12 inch die set at 0.010 inches and 500° F. was used to extrude low density polyethylene (USI, U.S. Industrial Chemicals, Division Nat'l Dist of Chemicals, 11500 Northlane Drive, Cincinnati, Ohio 45249, type NA344 resin) onto a forming structure rotating about the first stage forming drum (318). Due to the drawing of the web between the extruder and the forming structure, the initial thickness of the web when subjected to the first fluid pressure differential was about 0.001 inches. The forming structure in question exhibited apertures of three different diameters; 0.070 inches; 0.035 inches; and 0.010 inches. Web speed was 150 feet per minute. In the first stage, the larger capillary networks (1112 and 1115) were substantially formed and apertured, obtaining a high quality three-dimensional image of the forming structure. The smallest apertures (1111) were not formed in the first stage, for reasons previously described herein. As the macroscopically expanded film entered the second stage, it was subjected to a high pressure water jet (400) at 900 psig, 160° F, and 10 gallons per minute per cross-machine direction inch of web width. The nozzle (390), Spraying Systems Co., North Avenue at Schmale Road, Wheaton, Ill. 60189, #2520, was about 4 inches from the surface of the film. The smallest apertures (1111) were formed at this time. The resultant film contained capillary networks having the following approximate diameters: large (1115) 0.065 inches, medium (1112) 0.025 inches; and small (1111) less than about 0.005 inches. The overall no load caliper of the resultant web was approximately 0.040 inches.

EXAMPLE III

The macroscopically expanded, three-dimensional, apertured polymeric web 1210 shown in FIG. 16 was also made by the type of process generally disclosed in FIG. 6, but using a forming structure of the type generally disclosed in FIG. 11. The extruder and resin type were the same as described in Example II, above. All process operating conditions were substantially the same as those described in Example II, above, the primary difference being the forming structure. The forming structure was similar to that of FIG. 11, but with square debossments (856) having a 0.125 inch long sidewall. The debossments were 0.025 inches deep. The land areas were 0.025 inches in width. The perforate end wall (857) contained a multiplicity of small apertures (816), each measuring approximately 0.008 inches in diameter, with a density of 80 such apertures per linear inch in both directions. The film was macroscopically expanded in the first stage, forming approximately 0.025 inches deep capillary networks with closed end walls. The second stage of the process provided the small apertures (816) in the end walls of the capillary networks. The resultant macroscopically expanded, three-dimensional, apertured web exhibited square capillary networks (856) measuring approximately 0.120 inches on a side with apertures (816) measuring about 0.005 inches in their end walls.

While a number of particularly preferred embodiments in the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A continuous, multi-phase process for debossing and perforating a substantially continuous web of substantially planar polymeric film to form a macroscopically expanded, three-dimensional, apertured polymeric web, said process comprising the steps of:
    (a) continuously supporting said web of film on a forming structure exhibiting a multiplicity of fine-scale apertures which place the opposed surfaces of said forming structure in fluid communication with one another, said forming structure moving in a direction parallel to the direction of travel of said web of film and carrying said web of film in said direction;
    (b) substantially continuously applying a first fluid pressure differential across the thickness of said web of film along said direction of movement of said forming structure exhibiting said fine-scale apertures, said fluid pressure differential being sufficiently great to cause said web of film to rupture in those areas coinciding with said fine-scale apertures in said forming structure;
    (c) continuously supporting said finely apertured web of film on a forming structure exhibiting a macroscopic, three-dimensional, cross-section defined by a multiplicity of macroscopic cross-section apertures which place the opposed surface of said forming structure in fluid communication with one another, said forming structure moving in a direction parallel to the direction of travel of said web of film and carrying said web of film in said direction; and
    (d) substantially continuously applying a second fluid pressure differential across the thickness of said web of film along said direction of movement of said forming structure, said second fluid pressure differential being sufficiently great to cause said web of film to be urged into substantial conformance with the macroscopic, three-dimensional cross-section of said forming structure while substantially maintaining the integrity of said fine-scale apertures formed by said first fluid pressure differential.

2. The process of claim 1, wherein said fine-scale aperturing of said web and said macroscopic conformance of said web are performed on separate forming structures.

3. The process of claim 2, wherein said fine-scale aperturing of said web is carried out across the surface of said web on a first forming structure, said finely apertured web being thereafter fed from said first forming structure onto a second forming structure, where it is urged into conformance with the three-dimensional, macroscopic cross-section of said second forming structure.

4. The process of claim 2, wherein said second fluid pressure differential is sufficiently great to rupture said web in those areas coinciding with said macroscopic cross-section apertures in said forming structure.

5. The process of claim 3, wherein said web is fed onto said second forming structure so that the surface of the web which contacted said first forming structure does not contact said second forming structure.

6. The process of claim 5, wherein said web is transferred from said first forming structure to said second forming structure by passing it though a nip formed between said first and second forming structures.

7. The process of claim 1 wherein said fine scale aperturing of said web is carried out by directing a high pressure liquid jet at said web.

8. The process of claim 1, wherein said web is urged into substantial compliance with said forming structure exhibiting a macroscopic, three-dimensional cross-section by directing a high pressure liquid jet at said web.

9. The process of claim 1, wherein said web is urged into substantial compliance with said forming structure exhibiting a macroscopic, three-dimensional cross-section by subjecting the non-web contacting surface of said forming structure to vacuum.

10. The process of claim 1, wherein said web of substantially planar polymeric film is initially formed by extrusion of a resin melt.

11. The process of claim 1, wherein only a predetermined portion of said web is caused to rupture in those areas coinciding with said fine scale apertures.

12. The process of claim 1, wherein only a predetermined portion of said web is caused to substantially conform to said macroscopic, three-dimensional cross-section of said forming structure.

13. The process of claim 11 or claim 12, wherein an apertured mask element is interposed between said fluid pressure differential and said web to limit the portions of said web to be subjected to said fluid pressure differential to those areas coinciding with said apertures in said mask element.

14. The process of claim 6, wherein said fine scale apertures imparted to said web and said macroscopic, three-dimensional cross-section imparted to said web are maintained in register with one another by avoiding stretching of said web as it is transferred from said first forming structure to said second forming structure.

15. A continuous, multi-phase process for debossing and perforating a substantially continuous web of substantially planar polymeric film to form a macroscopically expanded, three-dimensional, apertured polyeric web, said process comprising the steps of:

(a) continuously supporting said web of film on a first forming structure exhibiting a multiplicity of fine-scale apertures which place the opposed surfaces of said forming structure in fluid communication with one another, said forming structure moving in a direction parallel to the direction of travel of said web of film and carrying said web of film in said direction;

(b) substantially continuously applying a first fluid pressure differential comprising a high pressure liquid jet across the thickness of said web of film along said direction of movement of said forming structure exhibiting said fine-scale apertures, the force applied by said fluid jet being sufficiently great to cause said web of film to rupture in those areas coinciding with said fine-scale apertures in said first forming structure;

(c) transferring said finely apertured web of film to a second forming structure exhibiting a macroscopic three-dimensional, cross-section defined by a multiplicity of macroscopic cross-section apertures which place the opposed surfaces of said second forming structure in fluid communication with one another, said second forming structure moving in a direction parallel to the direction of travel of said web of film and carrying said web of film in said direction; and (d) substantially continuously applying a second fluid pressure differential comprising a second high pressure liquid jet across the thickness of said web of film along said direction of movement of said second forming structure, said second fluid pressure differential being sufficiently great to cause said web of film to be urged into substantial conformance with the macroscopic, three-dimensional cross-section of said second forming structure and to rupture in those areas coinciding with said macroscopic cross-section apertures in said second forming sructure while substantially maintaining the integrity of said fine-scale apertures formed by said first fluid pressure differential in the areas of said web which are outside said macroscopic cross-section apertures.

16. The process of claim 15, wherein said web is fed onto said second forming structure so that the surface of the web which contacted said first forming structure does not contact said second forming structure.

17. The process of claim 15, wherein said web is transferred from said first forming structure to said second forming structure by passing it through a nip formed between said first and second forming structures.

18. The process of claim 15, wherein only a predetermined portion of said web is caused to substantially conform to said macroscopic three-dimensional cross-section of said second forming structure.

19. The process of claim 18, wherein an apertured mask element is interposed between said second high pressure fluid jet and said web to limit the portions of said web to be subjected to said second high pressure liquid jet to those areas coinciding with said apertures in said mask element.

20. A continuous, multi-phase process for debossing and perforating a substantially continuous web of substantially planar polymeric film to form a macroscopically expanded, three-dimensional, apertured polymeric web, said process comprising the steps of:

(a) continuously supporting said web of film on a forming structure exhibiting a multiplicity of fine-scale apertures which place the opposed surfaces of said forming structure in fluid communication and a macroscopic, three-dimensional cross-section defined by a multiplicity of macroscopic cross-section apertures which also place the opposed surfaces of said forming structure in fluid communication with one another, said forming structure moving in a direction parallel to the direction of travel of said web of film and carrying said web of film in said direction;

(b) substantially continuously applying a first fluid pressure differential comprising vacuum to the non-web contacting surface of said forming structure, thereby causing said web of film to be urged into substantial conformace with the macroscopic, three-dimensional cross-section of said forming structure and to rupture in those areas coinciding with said macroscopic cross-section apertures in said forming structure;

(c) substantially continuously applying a second fluid pressure differential comprising a high pressure liquid jet across the thickness of said web of film along said direction of movement of said forming structure, the force applied by said liquid jet being sufficiently great to cause said web of film to rupture in those areas coinciding with said fine-scale apertures in said forming structure while substantially maintaining the integrity of the macroscopic, three-dimensional configuration formed by said first fluid pressure differential.

21. The method of claim 20, wherein the temperature of said web is elevated to a molten state prior to subjecting said web to vacuum.

22. The process of claim 21, wherein said web of substantially planar polymeric film is initially formed by extrusion of a resin melt directly onto said forming structure.

23. The process of claim 21, wherein said web of film is cooled to its solid-state temperature prior to subjecting it to said second fluid pressure differential.

24. The process of claim 23, wherein said web is cooled by applying a low pressure liquid spray to the surface of said web while it is still subject to the vacuum utilized to apply said first fluid pressure differential.

25. A continuous, multi-phase process for debossing and perforating a substantially continuous web of substantially planar polymeric film to form a macroscopically expanded, three-dimensional, apertured polymeric web, said process comprising the steps of:

(a) continuously supporting said web of film on a forming structure exhibiting a macroscopic, three-dimensional cross-section defined by a multiplicity of macroscopic cross-section debossments having endwalls exhibiting a multiplicity of fine-scale apertures which place the opposed surfaces of said forming structure in fluid communication with one another, said forming structure moving in a direction parallel to the direction of travel of said web of film and carrying said web of film in said direction;

(b) substantially continuously applying a first fluid pressure differential comprising vacuum applied to the non-web contacting surface of said forming structure across the thickness of said web of film along said direction of movement of said forming structure, said fluid pressure differential being sufficiently great to cause said web of film to be urged into substantial conformance with the macroscopic, three-dimensional cross-section of said forming structure;

(c) substantially continuously applying a second fluid pressure differential comprising a high pressure liquid jet across the thickness of said web of film along said direction of movement of said forming structure, the force applied by said high pressure liquid jet being sufficiently great to cause said web of film to rupture in those areas coinciding with said fine-scale apertures in the endwalls of said debossments in said forming structure while substantially maintaining the integrity of the macroscopic, three-dimensional configuration formed by said first fluid pressure differential.

26. The process of claim 25, wherein said web of film is subjected to said first pressure differential while at a temperature above its solid-state temperature.

27. The process of claim 26, wherein said macroscopically expanded web is cooled below its molten temperature prior to subjecting it to said second fluid pressure differential.

28. The process of claim 27, wherein said cooling of said web is carried out by applying a low pressure cooling liquid spray thereto while said web is still subject to the vacuum comprising said first fluid pressure differential.

29. A continuous, multi-phase apparatus for debossing and perforating a substantially continuous web of substantially planar polymeric film to form a macroscopically expanded, three-dimensional, apertured polymeric web, said apparatus comprising:

(a) a first forming structure for continuously supporting said web of film, said first forming structure exhibiting a multiplicity of fine-scale apertures which place the opposed surfaces of said forming structure in fluid communication with one another;

(b) means for moving said first forming structure in a direction parallel to the direction of travel of said web of film;

(c) means for substantially continuously applying a first fluid pressure differential across the thickness of said web of film along said direction of movement of said first forming structure, said fluid pressure differential being sufficiently great to cause said web of film to rupture in those areas coinciding with said fine-scale apertures in said first forming structure;

(d) a second forming structure for continuously supporting said fine-scale apertured web of film, said second forming structure exhibiting a macroscopic, three-dimensional, cross-section defined by a multiplicity of macroscopic cross-section apertures which place the opposed surfaces of said second forming structure in fluid communication with one another;

(e) means for moving said second forming structure in a direction parallel to the direction of travel of said web of film; and (f) means for substantially continuously applying a second fluid pressure differential across the thickness of said web of film along said direction of movement of said second forming structure, said second fluid pressure differential being sufficiently great to cause said web of film to be urged into substantial conformance with the macroscopic, three-dimensional cross-section of said second forming structure and to rupture said web in those areas coinciding with said macroscopic cross-section apertures in said second forming structure while substantially maintaining the integrity of said fine-scale apertures formed by said first fluid pressure differential in the areas of said web which are outside said macroscopic cross-section apertures.

30. The apparatus of claim 29, including means for feeding said web onto said second forming structure so that the surface of the web which contacted said first forming structure does not contact said second forming structure.

31. The apparatus of claim 30, wherein said means for feeding said web from said first forming structure to said second forming structure comprises a nip formed between said first and second forming structures.

32. The apparatus of claim 29 wherein said means for applying said first fluid pressure differential across the thickness of said web comprises a high pressure liquid jet directed at said web.

33. The apparatus of claim 29, wherein said means for applying said second fluid pressure differential across the thickness of said web comprises a high pressure liquid jet directed at said web.

34. The apparatus of claim 32 or 33 wherein a vacuum chamber is positioned ajacent the non-web contacting surface of said forming structure, said vacuum chamber being aligned with said high pressure liquid jet to collect the liquid which penetrates said web.

35. The apparatus of claim 29, including extruder means for initially forming said substantially planar polymeric film from a resin melt.

36. The apparatus of claim 29, including an apertured mask element interposed between said second fluid pressure differential and said web to limit the portions of said web to be subjected to said second fluid pressure differential to those areas coinciding with said apertures in said mask element.

37. A continuous, multi-phase apparatus for debossing and perforating a substantially continuous web of substantially planar polymeric film to form a macroscopically expanded, three-dimensional, apertured polymeric web, said apparatus comprising:

(a) a forming structure for continuously supporting said web of film, said forming structure exhibiting a multiplicity of fine-scale apertures which place the opposed surfaces of said forming structure in fluid communication with one another and a macroscopic, three dimensional cross-section defined by a multiplicity of macroscopic cross-section apertures which also place the opposed surfaces of said forming structure in fluid communication with one another;

(b) means for moving said forming structure in a direction parallel to the direction of travel of said web of film;

(c) means for substantially continuously applying a first fluid pressure differential across the thickness of said web of film along said direction of movement of said forming structure, the force applied by said fluid pressure differential being sufficiently great to cause said web of film to be urged into substantial conformance with the macroscopic, three-dimensional cross-section of said forming structure and to rupture said web in those areas coinciding with said macroscopic cross-section apertures in said forming structure; and (d) means for substantially continuously applying a second fluid pressure differential across the thickness of said web of film along said direction of movement of said forming structure, said second fluid pressure differential being sufficiently great to rupture said web in those areas coinciding with said fine-scale apertures in said forming structure while substantially maintaining the integrity of the macroscopic, three-dimensional configuration formed by said first fluid pressure differential.

38. The apparatus of claim 37, wherein said means for applying said first fluid pressure differential across the thickness of said web comprises means for subjecting the non-web contacting surface of said forming structure to vacuum.

39. The apparatus of claim 37, wherein said means for applying said second fluid pressure differential across the thickness of said web comprises a high pressure liquid jet directed at said web.

40. The apparatus of claim 37, including means for elevating the temperature of said web to a molten state prior to subjecting said web to said first fluid pressure differential.

41. The apparatus of claim 40, wherein said means for elevating the temperature of said web to a molten state comprises an extruder.

42. The apparatus of claim 40, including means for cooling said web to its solid-state temperature prior to subjecting it to said fluid pressure differential.

43. The apparatus of claim 42, wherein said web cooling means comprises a low pressure liquid spray applied to the surface of said web while it is still subject to said first fluid pressure differential.

44. A continuous, mulit-phase apparatus for debossing and perforating a substantially continuous web of substantially planar polymeric film to form a macroscopically expanded, three-dimensional, apertured polymeric web, said apparatus comprising:
(a) a forming structure for continuously supporting said web of film, said forming structure exhibiting a macroscopic, three-dimensional cross-section defined by a multiplicity of macroscopic cross-section debossments having endwalls exhibiting a multiplicity of fine-scale apertures which place the opposed surfaces of said forming structure in fluid communication with one another;
(b) means for moving said forming structure in a direction parallel to the direction of travel of said web of film;
(c) means for substantially continuously applying a first fluid pressure differential comprising vacuum to the non-web contacting surface of said forming structure across the thickness of said web of film along said direction of movement of said forming structure, said fluid pressure differential being sufficiently great to cause said web of film to be urged into substantial conformance with the macroscopic, three-dimensional cross-section of said forming structure; and
(d) means for substantially continuously applying a second fluid pressure differential comprising a high pressure liquid jet across the thickness of said web of film along said direction of movement of said forming structure, the force applied by said high pressure liquid jet being sufficiently great to cause said web of film to rupture in those areas coinciding with said fine-scale apertures in the endwalls of said debossments in said forming structure while substantially maintaining the integrity of the macroscopic, three-dimensional configuration formed by said first fluid pressure differential.

45. The apparatus of claim 44, including means for elevating the temperature of said web above its solid-state temperature before it is subjected to said first fluid pressure differential.

46. The apparatus of claim 45, including means for cooling said macroscopically expanded web below to its solid-state temperature prior to subjecting it to said second fluid pressure differential.

47. The apparatus of claim 46, wherein said cooling means comprises a low pressure cooling liquid spray applied to said web while said web is still subject to said first fluid pressure differential.

* * * * *

UNITED STATES PATENT AND TRADEMARK OFFICE
CERTIFICATE OF CORRECTION

PATENT NO.  : 4,609,518

DATED       : September 2, 1986

INVENTOR(S) : John J. Curro, James C. Baird, Donald L. Gerth, George M. Vernon and E. Kelly Linman It is certified that error appears in the above-identified patent and that said Letters Patent is hereby corrected as shown below:

Title Page, under OTHER PUBLICATIONS, after "Resilient Structure.", insert --

European Patent Application No. 101082A published 2/22/84.
UK Patent Application GB 2 021 479 in the names of Garland Eugene Raley and James Michael Adams, published on 12/5/79.
UK Patent Application GB 2 103 933 in the name of George Howarth, published on 3/2/83. --.

Column 4, line 40, "characterists" should read -- characteristics --.

Column 8, line 8, "fabicated" should read -- fabricated --.

Column 12, line 4, "macroscopic" should read -- microscopic, --.

Column 17., line 1, "temperture" should read -- temperature --.

Column 22, line 11, after "to a" insert -- second --.

Column 22, line 21, "appriximately" should read -- approximately --.

Column 22, line 32, "4408" should read -- 44408 --.

Column 23, line 57, "surface" should read -- surfaces --.

Column 24, line 67, "polyeric" should read -- polymeric --.

Column 25, line 40, "sructure" should read -- structure --.

UNITED STATES PATENT AND TRADEMARK OFFICE
CERTIFICATE OF CORRECTION

PATENT NO. : 4,609,518

DATED : September 2, 1986

INVENTOR(S) : John J. Curro, James C. Baird, Donald L. Gerth, George M. Vernon and E. Kelly Linman It is certified that error appears in the above-identified patent and that said Letters Patent is hereby corrected as shown below:

Column 28, line 25, "ajacent" should read -- adjacent --.

Column 29, line 32, "mulit-phase" should read -- multi-phase --.

Signed and Sealed this

Tenth Day of March, 1987

Attest:

DONALD J. QUIGG

Attesting Officer

Commissioner of Patents and Trademarks